"""

US007485311B2

(12) United States Patent
Lue et al.

(10) Patent No.: US 7,485,311 B2
(45) Date of Patent: Feb. 3, 2009

(54) METHODS AND COMPOSITIONS FOR PREVENTING AND TREATING MALE ERECTILE DYSFUNCTION

(75) Inventors: Tom F. Lue, Hillsborough, CA (US); Ching-Shwun Lin, San Mateo, CA (US); Yuet W. Kan, San Francisco, CA (US)

(73) Assignee: Regents of the University of California, Oakland, CA (US)

( * ) Notice: Subject to any disclaimer, the term of this patent is extended or adjusted under 35 U.S.C. 154(b) by 323 days.

(21) Appl. No.: 10/806,515

(22) Filed: Mar. 22, 2004

(65) Prior Publication Data

US 2004/0180830 A1    Sep. 16, 2004

Related U.S. Application Data

(62) Division of application No. 09/909,544, filed on Jul. 19, 2001, now Pat. No. 6,852,323.

(60) Provisional application No. 60/220,031, filed on Jul. 21, 2000.

(51) Int. Cl.
*A61K 38/16* (2006.01)
(52) U.S. Cl. .................. 424/198.1; 530/399
(58) Field of Classification Search .............. None
See application file for complete search history.

(56) References Cited

U.S. PATENT DOCUMENTS

| | | | |
|---|---|---|---|
| 5,026,839 A | 6/1991 | Moscatelli et al. ............. 536/27 |
| 5,130,418 A | 7/1992 | Thompson ................. 530/399 |
| 5,155,214 A | 10/1992 | Baird et al. ................. 530/399 |
| 5,180,820 A | 1/1993 | Barde et al. ............... 536/23.51 |
| 5,188,943 A | 2/1993 | Florkiewicz et al. ........ 435/69.4 |
| 5,217,954 A | 6/1993 | Foster et al. ................. 514/12 |
| 5,229,500 A | 7/1993 | Barde et al. ................. 530/399 |
| 5,235,043 A | 8/1993 | Collins et al. ................. 530/399 |
| 5,270,053 A | 12/1993 | Schneider et al. ........... 424/450 |
| 5,387,673 A | 2/1995 | Seddon et al. ............... 530/399 |
| 5,438,121 A | 8/1995 | Barde et al. ................. 530/399 |
| 5,552,157 A | 9/1996 | Yagi et al. ................... 424/450 |
| 5,589,377 A | 12/1996 | Lebkowski et al. ......... 435/369 |
| 5,607,918 A | 3/1997 | Eriksson et al. ............... 514/12 |
| 5,646,181 A | 7/1997 | Fung et al. ................... 514/12 |
| 5,662,931 A | 9/1997 | Munechika et al. .......... 424/450 |
| 5,686,102 A | 11/1997 | Gross et al. ................. 424/450 |
| 5,693,531 A | 12/1997 | Chiorini et al. ............. 435/325 |
| 5,736,154 A | 4/1998 | Fuisz .......................... 424/449 |
| 5,741,511 A | 4/1998 | Lee et al. .................... 424/449 |
| 5,753,500 A | 5/1998 | Shenk et al. ............. 435/320.1 |
| 5,770,228 A | 6/1998 | Edwards et al. |
| 5,770,606 A | 6/1998 | El-Rashidy et al. |
| 5,830,725 A | 11/1998 | Nolan et al. ................. 435/455 |
| 5,886,039 A | 3/1999 | Kock et al. ............. 252/301.4 R |
| 5,891,915 A | 4/1999 | Wysor et al. ................. 514/573 |
| 5,939,096 A | 8/1999 | Clerc et al. .................. 424/450 |
| 5,941,868 A | 8/1999 | Kaplan et al. |
| 5,942,545 A | 8/1999 | Samour et al. ............... 514/573 |
| 5,945,117 A | 8/1999 | El-Rashidy et al. .......... 424/430 |
| 5,981,225 A | 11/1999 | Kochanek et al. ........... 435/69.1 |
| 5,986,070 A | 11/1999 | Collins et al. ............... 530/404 |
| 5,994,128 A | 11/1999 | Fallaux et al. ............... 435/325 |
| 6,007,838 A | 12/1999 | Alving et al. ................ 424/450 |
| 6,031,002 A | 2/2000 | Wysor et al. ................. 514/573 |
| 6,037,320 A | 3/2000 | Rosenthal |
| 6,056,966 A | 5/2000 | Selim et al. .................. 424/401 |
| 6,063,622 A | 5/2000 | Chamberlain et al. ........ 435/369 |
| 6,077,829 A | 6/2000 | Tanaka et al. .................. 514/21 |
| 6,083,750 A | 7/2000 | Chamberlain et al. ........ 435/369 |
| 6,120,798 A | 9/2000 | Allen et al. .................. 424/450 |
| 6,133,026 A | 10/2000 | Huang et al. ............. 435/320.1 |
| 6,193,992 B1 | 2/2001 | El-Rashidy et al. .......... 424/430 |
| 6,197,333 B1 | 3/2001 | Onyuksel et al. ............ 424/450 |
| 6,197,801 B1 | 3/2001 | Lin ............................ 514/365 |

(Continued)

FOREIGN PATENT DOCUMENTS

WO    WO00/43029    7/2000

(Continued)

OTHER PUBLICATIONS

Goldstein, 2000, International Journal of Impotence Research, 12, supp. 4, S152-S157.*

(Continued)

*Primary Examiner*—Celine X Qian
(74) *Attorney, Agent, or Firm*—Morrison & Foerster LLP

(57) ABSTRACT

This invention relates generally to the field of urology. In particular, the invention provides a method for preventing or treating male erectile dysfunction or female sexual arousal disorder, which method comprises administering an effective amount of vascular endothelial growth factor (VEGF), brain-derived neurotrophic factor (BDNF), basic fibroblast growth factor (bFGF), or a functional derivative or fragment thereof, or a nucleic acid encoding said VEGF, BDNF or bFGF, or functional derivative or fragment thereof, or an agent that enhances production and/or erection or sexual arousal stimulating function of said VEGF or BDNF or bFGF to a mammal, wherein such prevention or treatment is desirable, thereby preventing or treating said male erectile dysfunction or female sexual arousal disorder in said mammal. Combinations, combinatorial methods and kits for preventing or treating male erectile dysfunction or female sexual arousal disorder are also provided.

16 Claims, 8 Drawing Sheets

U.S. PATENT DOCUMENTS

| | | | |
|---|---|---|---|
| 6,221,646 B1 | 4/2001 | Dwarki et al. | 435/235.1 |
| 6,251,871 B1 | 6/2001 | Jin et al. | 514/44 |
| 6,258,374 B1 | 7/2001 | Friess et al. | 424/430 |
| 6,436,944 B1 | 8/2002 | Maytom | 514/258 |
| 2002/0032153 A1 | 3/2002 | Whitehouse | |

FOREIGN PATENT DOCUMENTS

| | | |
|---|---|---|
| WO | WO-00/72871 A1 | 12/2000 |
| WO | WO01/24809 | 4/2001 |
| WO | WO01/68125 | 9/2001 |

OTHER PUBLICATIONS

"Cialis Filed in European Union for Once-a-Day Dosing for Erectile Dysfunction," Business Wire via NewsEdge Corp. (Jun. 7, 2006).
"Erectile dysfunction is reversed by angiogenic gene therapy in hypercholesterolemia models," Angiogenesis Weekly via NewsEdge Corp. (Jun. 9, 2006).
"Erectile dysfunction models benefit from intracavernosal basic fibroblast growth factor," Angiogenesis Weekly via NewsEdge Corp. (May 5, 2006).
"Research from the United States in diabetes provides new insights," Diabetes Week via NewsEdge Corp. (May 8, 2006).
Basson et al., Journal of Sex & Marital Therapy (2001) 27:83-94.
Musicki et al., Mol. Pharmacol. (2005) 68:226-232.
Bakircioglu, J. Urol. (2001) 165:2103-2109.
Hanahan, Science (1997) 277:48-50.
Lee et al., J. Urol. (2002) 167:761-767.
Achen, et al., Proc. Nat'l. Acad. Sci. USA, 95(2): 548-553 (1998).
Alm, et al., Acta Physiol. Scand. 148: 421 (1993).
Anthony, et al., Placenta, 15: 557 (1994).
Asahara, et al., Circulation, 91(11): 2793-801 (1995).
Azadzoi, K.M. and I. Saenz de Tejada, Journal of Urology, 146(1): p. 238-40 (1991).
Baffour, et al., J. Vasc. Surg., 16: 181 (1992).
Bakircioglu et al., Journal of Urology, 163(4): 198 (2000).
Banai, et al., Circulation, 89(5): 2183-9 (1994).
Baumgartner, et al., Circulation, 97(12): 1114-23 (1998).
Bauters, C., et al., Am. J. Physiol., 267(4 Pt 2): H1263-71 (1994).
Bauters, et al., Circulation, 91(11): 2802-9 (1995).
Brown, et al., Lab. Invest., 76: 245 (1997).
Burchardt, et al., Biol. Reprod., 60(2): 398 (1999).
Burchardt, et al., IUBMB Life, 48: 405 (1999).
Carrier, et al., J. Urol., 153: 1722 (1995).
Cheung, et al., Am. J. Obstet. Gynecol., 173: 753 (1995).
Christ, G. J., Urol Clin North Am, 22:, 727 (1995).
Claffey, et al., J. Biol. Chem., 267: 16317 (1992).
Couper, et al., Circ. Res., 81: 932 (1997).
Current Protocols in Molecular Biology, Ausubel, et al. eds., John Wiley & Sons, Inc. (2000), Sambrook, et al., Molecular Cloning: A Laboratory Manual, Cold Spring Harbor Laboratory press, (1989).
Current Protocols in Molecular Biology, Ausubel, et al. eds., John Wiley & Sons Press, Chapters 9 and 16 (2000).
D'Amore, et al., Ann. Rev. Physiol., 49(9-10): 453-64 (1987).
DiStefano, et al., Neuron, 8:983 (1992).
Dong, J. Y., Fan, P. D. & Frizzell, R. A., Hum Gene Ther, 7:, 2101 (1996).
During, M. J. and Leone, P., Clin. Neurosci., 3: 292 (1995).
Dvorak, H.F., et al., Current Topics in Microbiology and Immunology, 237(1): p. 97-132 (1999).
El-Sakka, et al., J. Urol., 160: 2245 (1998).
Ferrara, N., Breast Cancer Research and Treatment, 36(2): p. 127-37 (1995).
Ferrara, N., et al., Endocr Rev, 13: 18 (1992).
Folkman, et al., Proc. Nat'l. Acad. Sci., 76(10): 5217-21 (1979).
Folkman, J. and Y. Shing, Journal of Biological Chemistry, 267(16): p. 10931-4 (1992).
Franck-Lissbrant, I., et al.,. Endocrinology, 139:, 451 (1998).
Garban, H., Marquez, D., Cai, L. et al., Biol Reprod, 53:, 1365 (1995).
Gimenez y Ribotta, et al., J. Neurosci. Res., 48: 281 (1997).
Goldberg, et al., J. Biol. Chem., 269: 4355 (1994).
Goldstein, et al., JAMA, 251(7):903-910 (1984).
Goldstein, International Journal of Impotence Research (2000) 12(4): S152-157.
Goodman & Gilman, Pharmacological Basis Of Therapeutics, 9th ed., McGraw-Hill Press (1996), p. 77-101.
Gross, et al., Proc. Nat'l. Acad. Sci., 80(9): 2623-27 (1983).
Grosskreutz, et al., Microvasc. Res., 58: 128 (1999).
Haggstrom, S., Wikstrom, P., Bergh, A. et al., Prostate, 36:, 71 (1998).
Haggstrom, S., Lissbrant, I. F., Bergh, A. et al,. J Urol, 161:, 1620 (1999).
Harada, K., et al., American Journal of Physiology, 270(5 Pt 2): p. H1791-802 (1996).
Hariawala, et al., J. Surg. Res., 63(1): 77-82 (1996).
Hatzichristou, D. G., Saenz de Tejada, I., Kupferman, S. et al., J Urol, 153:, 1126 1995.
Heaton, J.P., et al., Int'l J. Impotence Res., 8(1): 35-39 (1996).
Hopkins, et al., J. Vascular Surgery, 27(5): 886-94 (1998).
Houck, K.A., et al., J. Biol. Chem., 267(36): p. 26031-7 (1992).
Ide, Neurosci. Res., 25: 101 (1996).
Jin KL, Mao XO, Greenberg DA., Proc Natl Acad Sci U S A. 97:10242-7 (2000).
Jingjing, et al., Ophthamol. Vis. Sci., 40: 752 (1999).
Joukov, et al., EMBO J., 15: 1571 (1996).
Joukov, et al., EMBO J., 15(2):290-298 (1996).
Jung, et al., J. Urol., 160: 1899 (1998).
Jung, et al., Int. J. Impotence Res., 11: 247 (1999).
Karadeniz, T.,. et al., Urol Int, 55:, 143 (1995).
Karadeniz, et al., Urol. Int., 57: 85 (1996).
Kawasuji, et al., Ann. Thorac. Surg., 69: 1155 (2000).
Kim, J.H., et al., Journal of Urology, 151(1): p. 198-205 (1994).
Kornowski, et al., Circulation, 101: 545-48 (2000).
Korsching, J. Neurosci., 13: 2739 (1993).
Laham, et al., J. Am . Coll. Cardiol., 36: 2132-39 (2000).
Laham, et al., Curr. Interv. Cardiol. Rep., 1: 228 (1999).
Lazarous, et al., J. Am. Coll. Cardiol., 36: 1239 (2000).
Lee, et al., J. Urol. 163(4), 198 (2000).
Lei, et al., Biochim. Biophys. Acta, 1443: 400 (1998).
Leibrock, et al., Nature, 341: 149 (1989).
Lekas, E., Johansson, M., Widmark, A. et al., Urol Res, 25:, 309 (1997).
Leung, et al., Science, 246: 1306-09 (1989).
Levine, F.J., et al., J. Urology, 144(5): 1147-53 (1990).
Lewin and Barde, Ann. Rev. Neurosci., 19: 289 (1996).
Lin, et al., Proc. Nat'l Acad. Sci. USA, 97: 10242-47 (2000).
Liu, et al., J. Urol., 166: 354-360 (2001).
Losordo, et al., Am. Heart J., 138(2 Pt 2): 132-41 (1999).
Lue, T.F. New Eng. J. Med. 342(24), 1802-1813 (2000).
Maeda, Y., Ikeda, U., Ogasawara, Y. et al., Cardiovasc Res, 35:, 514, (1997).
Maglione, et al., Oncogene, 8: 925 (1993).
Magovern, C.J., et al., Human Gene Therapy, 8(2): p. 215-27 (1997).
Mannino and Gould-Fogerite, Bio Techniques, 6:682 (1988).
Matsushita, et al., Gene Ther. 5: 938 (1998).
McLaughlin, et al., J. Virol. 62: 1963 (1988).
Meisel, R. L., O'Hanlon, J. K. & Sachs, B. D., Horm Behav, 18:, 56 (1984).
Mersdorf, et al., J. Urol., 154: 749 (1991).
Meyer, et al., J. Cell Biol., 119: 45 (1992).
Miller, et al., [published erratum appears in Blood Feb. 1, 1995;85(3):862]. Blood. 82: 1900 (1993).
Mills, T. M., Lewis, R. W. & Stopper, V. S., Biol Reprod, 59: 1413 (1998).
Mills, T. M., Stopper, V. S. & Wiedmeier, V. T,. Biol Reprod, 51: 234 (1994).
Mills, T. B., Dai, Y., Stopper, V. S. et al., 64: 605 (1999).
Nehra, et al., J. Urol., 156: 1320 (1996).
Neufeld, et al., FASEB J., 13(1):9-22 (1999).
Nonomura, et al., Brain Res., 683: 129 (1995).
Ohara, et al., Gene Ther., 8: 837 (2001).
Olofsson, et al., Proc. Nat'l. Acad. Sci. USA, 93: 2576 (1996).
Oppenheim, et al., Nature, 360: 755 (1992).
Ortega, et al., Front. Biosci. 4(4):D141-152 (1999).

Paick et al., Urology, 42: 145 (1993).
Park et al., Int'l J. Impotence Res., 9(1): 27-37 (1997).
Parker, et al., Steroid Biochem, 6:, 1, (1975).
Podsakoff, et al., J. Virol. 68: 5656, (1994).
Poltorak, et al., J. Biol. Chem., 272(11): 7151-78 (1997).
Pueyo, et al., Exp. Cell Res., 238: 354 (1998).
Quantin, et al., Proc. Natl. Acad. Sci. USA, 89:2581-2584 (1992).
Rajanayagam, et al., J. Am. Coll. Cardiol., 35: 519 (2000).
Rakue, et al., Japan Circ. J., 62: 933-39 (1998).
Rosen, M.P., et al., Radiology, 174(3 Pt 2): 1043-48 (1990).
Rosenfeld, et al., Cell, 68:143-155 (1992).
Shweiki, et al., Proc. Nat'l Acad. Sci. USA, 92: 768 (1995).
Sondell, et al., Eur. J. Neurosci., 12: 4243-54 (2000).
Stenberg, P. E., Shuman, M. A., Levine, S. P. et al., J Cell Biol, 98: 748 (1984).
Stratford-Perricadet, et al., J. Clin. Invest., 90:626-630 (1992).
Symes, et al., Ann. Thorac. Surg., 68: 830 (1999).
Takeshita, et al., Am. J. Path., 147(6): 1649-60 (1995).
Takeshita, et al., J. Clin. Invest., 93(2): 662-70 (1994).
Takeshita, et al.,Circulation, 90(5 Pt 2): II228-34 (1994).
Tischer, et al., J. Biol. Chem., 266: 11947 (1991).
Unger, et al., Am. J. Cardiol., 85: 1414-19 (2000).
Verdonck, A., De Ridder, L., Arch Oral Biol, 43:, 551 (1998).
Walder, C.E., et al., Journal of Cardiovascular Pharmacology, 27(1): p. 91-8 (1996).
Walsh, et al., Br. J. Urol., 56: 694 (1984).
Waltenberger, et al., J. Biol. Chem., 269: 26988 (1994).
Watson et al. Molecular Biology of the Gene, 4th Edition, The Bejacmin/Cummings Pub. co., p. 224 (1987).
Yamada, et al., Genomics, 42: 483 (1997).
Yan, et al., Nature, 360: 753 (1992).
Zheng, et al., Am. J. Physiol. Heart Circ. Physiol., 280: H909-17 (2001).
Zvara, P., Sioufi, R., Schipper, H. M. et al., Int J Impot Res, 7: 209 (1995).
Gholami et al., Journal of Urology (2002) 167(4) Suppl.:235.
Baskin et al., The Journal of Urology (1999) 162:1015-1020.
Berman et al., The Journal of Urology (2003) 170:2333-2338.
Burnett et al., The Journal of Urology (1997) 158:75-78.
Chattopadhyay et al., Gene Therapy (2005) 12:1377-1384.
Dasgupta et al., The Journal of Urology (2004) 171:1189-1193.
Gholami et al., The Journal of Urology (2003) 169:1577-1581.
Gray's Anatomy, 38th ed., (1999) Chapter 3: Embryology and Development, Reproductive System, pp. 210, 214-216.
Melman, International Journal of Impotence Research (2006) 18:19-25.
Musicki et al., Biology of Reproduction (2004) 70:282-289.
Pessina et al., Endocrinology (2006) 147:61-69.
Rehman and Melman, The Journal of Urology (1999) 161:200-206.
Viagra (sildenafil citrate) http://www.viagra.com/ web page visited Apr. 6, 2006.
Yilmaz et al., The Journal of Urology (2002) 167:616-620.
Yoon, et al., International Journal of Impotence Research (2005) 17:33-38.
Zippe et al., International Journal of Impotence Research (2006) 18:1-18.
Purves et al., Neuroscience, 2nd Edition (2001) Sinauer Associates, Inc.
Goto et al., Lab. Inves. (1993) 69:508-517.
Te, Alexis E. et al. "Neurotrophic Factors in the Rat Penis", *Journal of Urology*, vol. 152, pp. 2167-2172, (1994).
Folkman, Judah, MD, "Clinical Applications of Research on Angiogenesis", *The New England Journal of Medicine*, vol. 333, pp. 1757-1763, (1995).

\* cited by examiner

VASCULAR ENDOTHELIAL GROWTH FACTOR PROMOTES CAVERNOUS SMOOTH MUSCLE CELLS

METHODS AND COMPOSITIONS FOR PREVENTING AND TREATING MALE ERECTILE DYSFUNCTION

CROSS-REFERENCE TO RELATED APPLICATIONS

This application is a divisional of U.S. application Ser. No. 09/909,544, filed Jul. 19, 2001, which claims the benefit of the priority date of U.S. provisional patent application Ser. No. 60/220,031, filed Jul. 21, 2000, under 35 U.S.C. § 119(e). The disclosures of the above-described applications are incorporated herein by reference in their entirety.

STATEMENT OF RIGHTS TO INVENTIONS MADE UNDER FEDERALLY SPONSORED RESEARCH

This invention is supported by Grant No. DK45370 and DK51374 of the National Institutes of Health. The United States government may have certain rights in this invention. The disclosure of the above-described application is incorporated herein by reference in its entirety.

FIELD OF INVENTION

This invention relates generally to the field of urology. In particular, the invention provides a method for preventing or treating male erectile dysfunction or female sexual arousal disorder, which method comprises administering an effective amount of vascular endothelial growth factor (VEGF), brain-derived neurotrophic factor (BDNF), basic fibroblast growth factor (bFGF), or a functional derivative or fragment thereof, or a nucleic acid encoding said VEGF, BDNF or bFGF, or functional derivative or fragment thereof, or an agent that enhances production and/or said male erection or female sexual arousal stimulating function of said VEGF or BDNF or bFGF to a mammal, wherein such prevention or treatment is desirable, thereby preventing or treating said male erectile dysfunction or said female sexual arousal disorder in said mammal. Combinations, kits, and combinatorial methods for preventing or treating male erectile dysfunction or female sexual arousal disorder are also provided.

BACKGROUND OF INVENTION

VEGF is a family of proteins that were discovered on the basis of their ability to stimulate VEC growth (angiogenesis). It now comprises five members, namely, VEGF-A, VEGF-B, VEGF-C, VEGF-D, and PLGF (placenta growth factor) that are encoded from distinct genes. Achen, et al., *Proc. Nat'l. Acad. Sci. USA*, 95: 548 (1998), Joukov, et al., *EMBO J*, 15: 1571 (1996), Maglione, et al., *Oncogene*, 8: 925 (1993), Olofsson, et al., *Proc. Nat'l. Acad. Sci. USA*, 93: 2576 (1996), Yamada, et al., *Genomics*, 42: 483 (1997). Each of the five members in turn comprises two or more isoforms that arise by the splicing of their respective pre-mRNAs. For example, the VEGF-A family includes $VEGF_{206}$, $VEGF_{189}$, $VEGF_{183}$, $VEGF_{165}$, $VEGF_{145}$, $VEGF_{121}$, and $VEGF_{111}$. Anthony, et al., *Placenta*, 15: 557 (1994), Neufeld, et al., *FASEB J.*, 13: 9 (1999), Lei, et al., *Biochim. Biophys. Acta*, 1443: 400 (1998), Jingjing, et al., *Ophthamol. Vis. Sci.*, 40: 752 (1999), Cheung, et al., *Am. J. Obstet. Gynecol.*, 173: 753 (1995), Burchardt, et al., *Biol. Reprod.*, 60: 398 (1999). Among all VEGF proteins and isoforms, $VEGF_{165}$ is by far the most frequently used form of VEGF both in basic and clinical studies.

It has been shown that, among different vascular cell types (endothelial, smooth muscle cells (SMC), and fibroblasts), SMC is the principal source for the secreted VEGF. Pueyo, et al., *Exp. Cell Res.*, 238: 354 (1998). Expression of VEGF in SMC is upregulated by multiple factors including phorbol esters (Tischer, et al., *J. Biol. Chem.*, 266: 11947 (1991)), cAMP (Claffey, et al., *J. Biol. Chem.*, 267: 16317 (1992)), and hypoxia (Goldberg, et al., *J. Biol. Chem.*, 269: 4355 (1994), Shweiki, et al., *Proc. Nat'l Acad. Sci. USA*, 92: 768 (1995)). The secreted VEGF acts on VEC principally through two different cell surface receptors, VEGFR-1 and VEGFR-2. Activation of VEGFR-1 results in VEC migration, while activation of VEGFR-2 VEC migration and proliferation. Waltenberger, et al., *J. Biol. Chem.*, 269: 26988 (1994), Neufeld, et al., *FASEB J.*, 13: 9 (1999), Ortega, et al., *Front. Biosci.*, 4: D141 (1999). Although VEGFR-1 and VEGFR-2 have long been considered endothelium-specific, they have both been detected in human uterine and bovine aorta SMC. Grosskreutz, et al., *Microvasc. Res.*, 58: 128 (1999), Brown, et al., *Lab. Invest.*, 76: 254 (1997). Cultured uterine SMC responded to VEGF in the form of cell proliferation and cultured aorta SMC cell migration. Cultured human colon SMC, however, did not express VEGF receptors, nor did they respond to VEGF treatment. Brown, et al., *Lab. ////Invest.*, 76: 254 (1997).

Angiogenesis is a complex process that includes activation, migration and proliferation of endothelial cells and formation of new blood vessels. D'Amore, et al., *Ann. Rev. Physiol.*, 49(9-10): 453-64 (1987). VEGF has been shown to be intimately involved in the entire sequence of events leading to growth of new blood vessels. Gross, et al., *Proc. Nat'l. Acad. Sci.*, 80(9): 2623-27 (1983), Folkman, et al., *Proc. Nat'l. Acad. Sci.*, 76(10): 5217-21 (1979). Five human VEGF isoforms of 121, 145, 165, 189 and 206 amino acids have been isolated. Gross, et al., *Proc. Nat'l. Acad. Sci.*, 80(9): 2623-27 (1983), Leung, et al., *Science*, 246: 1306-09 (1989), Poltorak, et al., *J. Biol. Chem.*, 272(11): 7151-78 (1997). Among the isoforms, VEGF 165 seems to be the most effective and most commonly used. The effect of VEGF 165 in augmenting perfusion and in stimulating formation of collateral vessels has been shown in animal models Hopkins, et al., *J. Vascular Surgery*, 27(5): 886-94 (1998), Asahara, et al., *Circulation*, 91(11): 2793-801 (1995), Hariawala, et al., *J. Surg. Res.*, 63(1): 77-82 (1996), Bauters, et al., *Circulation*, 91(11): 2802-9 (1995), Bauters, C., et al., *Am. J. Physiol.*, 267(4 Pt 2): H1263-71 (1994), Takeshita, et al., *J. Clin. Invest.*, 93(2): 662-70 (1994), Takeshita, et al., *Circulation*, 90(5 Pt 2): II228-34 (1994), Takeshita, et al., *Am. J. Path.*, 147(6): 1649-60 (1995), Banai, et al., *Circulation*, 89(5): 2183-9 (1994). In clinical trials, successful induction of collateral blood vessels in ischemic heart disease and critical limb ischemia by VEGF have also been reported. Baumgartner, et al., *Circulation*, 97(12): 1114-23 (1998), Losordo, et al., *Am. Heart J.*, 138(2 Pt 2): 132-41 (1999).

Neurotrophins are a class of structurally related growth factors that promote neural survival and differentiation. They stimulate neurite outgrowth, suggesting that they can promote regeneration of injured neurons, and act as target-derived neurotrophic factors to stimulate collateral sprouting in target tissues that produce the neurotrophin. Korsching, *J. Neurosci.*, 13: 2739 (1993). Recently, local synthesis and autocrine mechanisms of action have been reported. Lewin and Barde, *Ann. Rev. Neurosci.*, 19: 289 (1996). In vivo overexpression of a neurotrophic factor, through gene transfer, would ensure local and continuous neurotrophin production in a manner resembling the physiologic, as these proteins are usually produced and secreted by target and glial cells surrounding neurons.

Brain-derived neurotrophic factor (BDNF) was initially characterized as a basic protein present in brain extracts and capable of increasing the survival of dorsal root ganglia. Leibrock, et al., *Nature,* 341: 149 (1989). When axonal communication with the cell body is interrupted by injury, Schwann cells produce neurotrophic factors such as nerve growth factor (NGF) and BDNF. Neurotrophins are released from the Schwann cells and dispersed diffusely in gradient fashion around regenerating axons, which then extend distally along the neurotrophins' density gradient. Ide, *Neurosci. Res.,* 25: 101 (1996). Local application of BDNF to transected nerves in neonatal rats has been shown to prevent the massive death of motor neurons that follows axotomy. DiStefano, et al., *Neuron,* 8:983 (1992), Oppenheim, et al., *Nature,* 360: 755 (1992), Yan, et al., *Nature,* 360: 753 (1992). The mRNA titer of BDNF increases to several times the normal level 4 days after axotomy and reaches its maximum at 4 weeks. Meyer, et al., *J. Cell Biol.,* 119: 45 (1992). Moreover, BDNF has been reported to enhance the survival of cholinergic neurons in culture. Nonomura, et al., *Brain Res.,* 683: 129 (1995).

Basic fibroblast growth factor (bFGF) is a member of the fibroblast growth factor family. bFGF stimulates the proliferation of all cells of mesodermal origin including smooth muscle cells, neuroblasts, and endothelial cells. bFGF stimulates neuron differentiation, survival, and regeneration. In vitro functions suggest that bFGF modulates angiogenesis, wound healing and tissue repair, and neuronal function in vivo. bFGF, a heparin-binding growth factor, is capable of inducing functionally significant angiogenesis in models of myocardial and limb ischemia. Zheng, et al., *Am. J. Physiol. Heart Circ. Physiol.,* 280: H909-17 (2001), Laham, et al., *J. Am. Coll. Cardiol.,* 36: 2132-39 (2000), Laham, et al., *Curr. Interv. Cardiol. Rep.,* 1: 228 (1999), Unger, et al., *Am. J. Cardiol.,* 85: 1414-19 (2000), Kawasuji, et al., *Ann. Thorac. Surg.,* 69: 1155 (2000), Rajanayagam, et al., *J. Am. Coll. Cardiol.,* 35: 519 (2000), Kornowski, et al., *Circulation,* 101: 545-48 (2000), Ohara, et al., *Gene Ther.,* 8: 837 (2001), Lazarous, et al., *J. Am. Coll. Cardiol.,* 36: 1239 (2000), Rakue, et al., *Japan Circ. J.,* 62: 933-39 (1998), Baffour, et al., *J. Vasc. Surg.,* 16: 181 (1992).

Erectile function is a hemodynamic process of blood inflow and pressure maintenance in the cavernosal spaces. Christ, *Urol. Clin. North Am.,* 22: 727 (1995). Following sexual arousal and the release of nitric oxide to the erectile tissue, three processes occur to achieve an erection. These are relaxation of the trabecular smooth muscle, arterial dilation and venous compression. Id. During this final stage, arterial flow fills sinusoidal spaces, compressing subtunical venules thereby reducing venous outflow. Blood flows into the cavernous spaces of the penis, thus expanding and stretching the penis into a rigid organ. The flow of blood in and out of the cavernous spaces is controlled by cavernous smooth muscle cells (CSMC) embedded in the trabeculae of the cavernous spaces. With normal erectile function, a high intracavernous pressure (ICP) is maintained with a low inflow rate. Karadeniz, et al., *Urol. Int.,* 57: 85 (1996).

As such, the penis is a predominantly vascular organ, and vascular or penile arterial insufficiency is the most common etiology of erectile dysfunction (ED). Sinusoidal smooth muscle atrophy and collagen deposition is a common finding in men with long standing ED of various etiologies, whether due to hormonal, neurological or vascular causes. Karadeniz, et al., *Urol. Int.,* 57: 58 (1996). Such degradation in smooth muscle quantity and quality leads to veno-occlusive dysfunction. This represents an end-stage muscular degeneration akin to myocardial changes with congestive heart failure or dilated cardiomyopathy for which no treatment currently exists with hope of reversing the underlying pathologic process.

Veno-occlusive disease is a common finding among patients with erectile dysfunction (ED). Following radical prostatectomy, for example, approximately 30% of patients may have vasculogenic ED in addition to neurogenic ED and at least half of these men may have venous leak. Regardless of the etiology of organic ED (neurogenic, traumatic, hormonal, and vascular, etc.), venous leakage is a common final condition resulting from smooth muscle atrophy. Mersdorf, et al., *J. Urol.,* 154: 749 (1991). Veno-occlusive dysfunction is the most common etiology of ED among non-responders to medical management of ED. None of the medical therapy currently exists is curative for this condition. Patients with veno-occlusive dysfunction exhibit a poor response to intra-cavernous injection with vasoactive agents (papavarine, prostaglandin E1, phentolamine, or combinations, for example), despite good arterial flow demonstrated by duplex ultrasound. The diagnosis of veno-occlusive disease may be confirmed with specific findings on cavernosometry and cavernosography. Nehra, et al., *J. Urol.,* 156: 1320 (1996).

Atherosclerotic or traumatic arterial occlusive disease of the pudendal-cavernous-helicine arterial tree can decrease the perfusion pressure and arterial flow to the sinusoidal spaces, thus decreasing the rigidity of the erect penis. Common risk factors associated with generalized arterial insufficiency include hypertension, hyperlipidemia, cigarette smoking, diabetes mellitus, and pelvic irradiation. Goldstein, et al., *JAMA,* 251: 903-910 (1984), Rosen, M. P., et al., *Radiology,* 174(3 Pt 2): 1043-48 (1990), Levine, F. J., et al., *J. Urology,* 144(5): 1147-53 (1990). Epidemiological studies have shown a high incidence of ED in patients with coronary arterial disease. Heaton, J. P., et al., *Int'l J. Impotence Res.,* 8(1): 35-39 (1996). Focal lesion of the common penile or cavernous artery is most often seen in young patients who have sustained blunt pelvic or perineal trauma such as in cases of biking accidents. Levine, F. J., et al., *J. Urology,* 144(5): 1147-53 (1990).

Because of the close proximity of the cavernous nerves to the capsule of the prostate, ED is a frequent complication after radical prostatectomy or cystectomy and prostatic cryo-surgery. Although the nerve-sparing prostatectomy technique developed by Walsh, et al., *Br. J. Urol.,* 56: 694 (1984) has significantly reduced the postoperative impotence rate, a large number of patients still suffer from inadequate penile rigidity. Peripheral nerve regeneration is a slow process, and the fact that most patients do not recover potency for 6 months to 2 years indicates substantial axonal damage, even with preservation of the neural sheath. An anatomic study of the cavernous nerves by Paick et al., *Urology,* 42: 145 (1993) revealed both a medial and a lateral bundle of cavernous nerves at the level of the prostate, suggesting that in some cases the lateral bundle can be saved, even in non-nerve-sparing prostatectomy.

We have hypothesized that sprouting of the remaining nerves in penile tissue may be more important in regeneration than re-growth of nerves through the damaged and fibrotic tissues. This concept was confirmed in an animal study that revealed regeneration of the cavernous nerves after unilateral resection. Carrier, et al., *J. Urol.,* 153: 1722 (1995). In addition, a previous study in our laboratory showed that systemic growth hormone injection significantly enhanced cavernous nerve regeneration after unilateral injury. Jung, et al., *J. Urol.,* 160:1899 (1998).

Methods for treating erectile dysfunction have included from the administration of prostaglandin E (U.S. Pat. No. 5,942,545), local administration of vascular muscle relaxants and vasoactive pharmaceutical agents. See, for example, U.S. Pat. Nos. 5,942,545, 6,056,966; and 5,646,181.

Advancement in molecular biology has brought improved understanding of pathophysiology on the gene and molecular level, and offers promise of treatment possibilities aimed at a specific pathologic molecular mechanism. As in other vasculopathies such as limb claudication (Baumgartner, et al., *Circulation*, 97: 1114 (1998) and coronary artery disease (Symes, et al., *Ann. Thorac. Surg.*, 68: 830 (1999), treatment with VEGF in either protein or gene form has increased neovascularity in animal models and improved symptomatic angina and wound healing in humans with inoperable heart disease and critical limb ischemia, respectively. The penis represents a convenient tissue target for gene therapy due to the penis' external location on the body, ubiquity of endothelial-lined spaces and low-level blood flow in the flaccid state. In addition, the penis is filled with billions of endothelial and smooth muscle cells both are rich in VEGF receptors. Liu, et al., *J. Urol.*, 166: 354-360 (2001).

Recently, we have established an animal model in which CSMC was seen decreased following internal iliac artery ligation that restricted blood supply to the penis. However, rats treated with intracavernous injection of vascular endothelial growth factor (VEGF) shortly after internal iliac artery ligation had nearly normal CSMC. The protective effects of VEGF on CSMC could be due to partial restoration of blood supply as VEGF is expected to stimulate vascular endothelial cell (VEC) proliferation. Lin, et al., *Proc. Nat'l Acad. Sci. USA*, 97: 10242-47 (2000). Alternatively, VEGF might act directly on CSMC, as we will present evidence that CSMC express one of the two principal VEGF receptors. Sondell, et al., *Eur. J. Neurosci.*, 12: 4243-54 (2000).

Females can also have sexual dysfunction, and this dysfunction can increase with age. It is usually associated with the presence of vascular risk factors, genital smooth muscle atrophy, and onset of menopause. Some of the vascular and muscular mechanisms that contribute to penile erection in the male are believed to be similar vasculogenic factors in the female genital response. It is known that in women sexual arousal is accompanied by arterial inflow which engorges the vagina and increases vaginal lubrication, and that the muscles in the perineum assist in achieving clitoral erection.

In the female patient, sexual arousal disorder can arise from organic and pyschogenic causes, or from a combination of the foregoing. Female sexual arousal disorder is classified into five categories: 1) hypoactive sexual desire disorder, 2) sexual aversion disorder, 3) sexual arousal disorder, 4) orgasmic disorder, and 5) sexual pain disorder. The present invention applies to sexual arousal disorder. Sexual arousal disorder is the persistent or recurring inability to attain or maintain adequate sexual excitement, causing personal distress. It may be experienced as the lack of subjective excitement or the lack of genital lubrication or swelling or other somatic responses. Organic female sexual arousal disorder is known to be related in part to vasculogenic impairment resulting in inadequate blood flow, vaginal engorgement insufficiency and clitorial erection insufficiency. Animal studies have demonstrated the dependence of vaginal vascular engorgement and clitoral erection on blood flow. See, for example, Park et al., "Vasculogenic female sexual dysfunction: the hemodynamic basis for vaginal engorgement insufficiency and clitoral erectile insufficiency, "*Int'l J. Impotence Res.*, 9(1), 27-37 (March 1997).

Female sexual dysfunction has been treated with pharmacological intervention to stimulate blood flow as well as prostaglandins. See, for example, U.S. Pat. Nos. 6,193,992 B1; 5,945,117; 6,031,002; and 5,891,915.

SUMMARY OF INVENTION

In one aspect, the invention provides a method for preventing or treating male erectile dysfunction or female sexual arousal disorder, which method comprises administering to a mammal to whom such treatment is needed or desirable, an effective amount of: a) vascular endothelial growth factor (VEGF) or a functional derivative or fragment thereof, or a nucleic acid encoding said VEGF or functional derivative or fragment thereof, or an agent that enhances production and/or said male erection or female sexual arousal stimulating function of said VEGF; or b) brain-derived neurotrophic factor (BDNF) or a functional derivative or fragment thereof, or a nucleic acid encoding said BDNF or functional derivative or fragment thereof, or an agent that enhances production and/or said male erection or female sexual arousal stimulating function of said BDNF; or c) basic fibroblast growth factor (bFGF) or a functional derivative or fragment thereof, or a nucleic acid encoding said bFGF or functional derivative or fragment thereof, or an agent that enhances production and/or said male erection or female sexual arousal stimulating function of said bFGF, thereby preventing or treating said male erectile dysfunction or female sexual arousal disorder in said mammal.

Any mammal can treated with the present method. Preferably, a human is treated, and more preferably with VEGF, BDNF, bFGF peptides or nucleic acids, or a functional derivative or fragment thereof, that is of human origin.

VEGF, BDNF, bFGF or a functional derivative or fragment thereof, or nucleic acid encoding the VEGF, BDNF, bFGF, or a functional derivative or fragment thereof, or an agent that enhances production and/or the male erection or femal sexual arousal stimulating function of the VEGF or BDNF or bFGF can be administered by any methods known in the art. For example, the VEGF, BDNF or bFGF protein or nucleic acid, or a functional derivative or fragment thereof, can be administered by injection, and preferably by intracavernous injection, subcutaneous injection, intravenous injection, intramuscular injection, intradermal injection, or can be administered topically. The VEGF, BDNF or bFGF nucleic acid, or a functional derivative or fragment thereof, can be administered via a gene therapy vector susch as an adeno-associated virus, a retrovirus, an adenovirus, or a lentivirus vector. Preferably, the gene therapy vector will be an adenovirus-associated VEGF, BDNF or bFGF gene vector. One preferred embodiment would be the administration of AAV-VEGF, AAV-BDNF, or AAV-bFGF by intracaveronous injection of about 0.5 to 2.0 ml at a concentration of about $10^{10}$ viral titer. The VEGF, BDNF or bFGF protein, or a functional derivative or fragment thereof, or the VEGF, BDNF or bFGF nucleic acid, or a functional derivative or fragment thereof, can also be administered via a liposome.

Any form of male erectile or female sexual arousal disorder can be treated by the present method. For example, male erectile dysfunction (ED) caused by venous leakage can be treated or prevented. ED or female sexual arousal disorder caused by trauma or cavernous nerve injury can be treated or prevented. ED or female sexual arousal disorder secondary to nerve dysfunction, arterial insufficiency, hormonal insufficiency, surgery, radiation or chemotherapy can also be treated or prevented.

A preferred embodiment of the present invention administers a) VEGF or a functional derivative or fragment thereof, or a nucleic acid encoding said VEGF or functional derivative or fragment thereof, or an agent that enhances production and/or said female sexual arousal stimulating function of said VEGF; or b) BDNF or a functional derivative or fragment thereof, or a nucleic acid encoding said BDNF or functional derivative or fragment thereof, or an agent that enhances production and/or said female sexual arousal stimulating function of said BDNF; or c) bFGF or a functional derivative or fragment thereof, or a nucleic acid encoding said bFGF or functional derivative or fragment thereof, or an agent that enhances production and/or said female sexual arousal stimulating function of said bFGF, in an amount sufficient to improve blood flow and regenerate nerve and smooth muscle in the clitoris and vaginal wall. A preferred administration would be in a cream or via injection to the clitoris and vaginal wall of the patient.

Another preferred embodiment provides for the administration of the treatment for VEGF, BDNF, bFGF protein or nucleic acid, or some combination thereof by intracavernous injection.

One preferred embodiment is the administration of the VEGF, BDNF, or bFGF protein is administered at about 10-200 mcg/70 Kg body weight about once every two to six months.

In another aspect, the invention provides a combination for preventing or treating male erectile dysfunction or female sexual arousal disorder, which combination comprises: a) an effective amount of an agent that stimulates male erection or female sexual arousal; and b) one or more of the following: i) an effective amount of VEGF or a functional derivative or fragment thereof, or a nucleic acid encoding said VEGF or functional derivative or fragment thereof, or an agent that enhances the production and/or said male erection or female sexual arousal stimulating function of said VEGF; ii) an effective amount of BDNF or a functional derivative or fragment thereof, or a nucleic acid encoding said BDNF or functional derivative or fragment thereof, or an agent that enhances production and/or said male erection or female sexual arousal function stimulating function of said BDNF; or iii) an effective amount of bFGF or a functional derivative or fragment thereof, or a nucleic acid encoding said bFGF or functional derivative or fragment thereof, or an agent that enhances production and/or said male erection or female sexual arousal stimulating function of said bFGF.

VEGF, BDNF or bFGF proteins or functional derivatives or fragments thereof, or a nucleic acid encoding VEGF, BDNF or bFGF, or functional derivatives or fragments thereof, can be prepared by any methods known in the art, e.g., synthetic methods, recombinant methods or a combination thereof.

The formulation, dosage and route of administration of the above-described compositions, combinations, preferably in the form of pharmaceutical compositions, can be determined according to the methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of peptides and Proteins*, Hovgaard and Frkjr (Ed.), Taylor & Francis, Inc., 2000; *Medical Applications of Liposomes*, Lasic and Papahadjopoulos (Ed.), Elsevier Science, 1998; *Textbook of Gene Therapy*, Jain, Hogrefe & Huber Publishers, 1998; *Adenoviruses: Basic Biology to Gene Therapy*, Vol. 15, Seth, Landes Bioscience, 1999; *Biopharmaceutical Drug Design and Development*, Wu-Pong and Rojanasakul (Ed.), Humana Press, 1999; *Therapeutic Angiogenesis: From Basic Science to the Clinic*, Vol. 28, Dole et al. (Ed.), Springer-Verlag New York, 1999). The compositions, combinations or pharmaceutical compositions can be formulated for oral, rectal, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular composition, combination or pharmaceutical composition which is being used.

The above-described combinations, preferably in the form of pharmaceutical compositions, can be used for preventing or treating male erectile or female sexual arousal disorder. Said combinations can further comprise a pharmaceutically acceptable carrier or excipient. A kit which comprises said combinations and an instruction for using said combination in treating or preventing male erectile dysfunction or female sexual arousal disorder is also contemplated in the present invention.

DETAILED DESCRIPTION OF INVENTION

A. Definitions

Figure 1A:
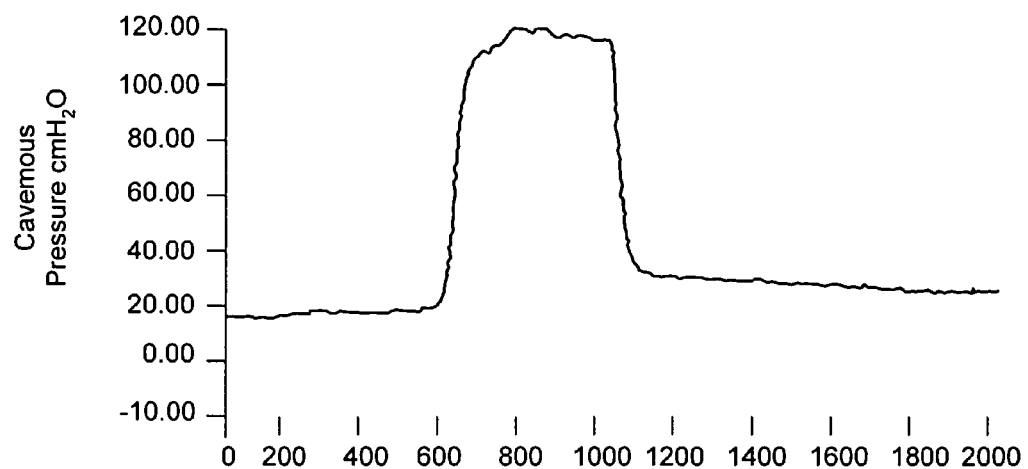
FIG. 1. Electrostimulation of the cavernous nerve at 8 weeks: A) sham operation group; B) LacZ group; and C) BDNF group. Note higher maximal intracavernous pressure in the BDNF than in the LacZ group. Scan rate=10/sec.
Figure 1A:
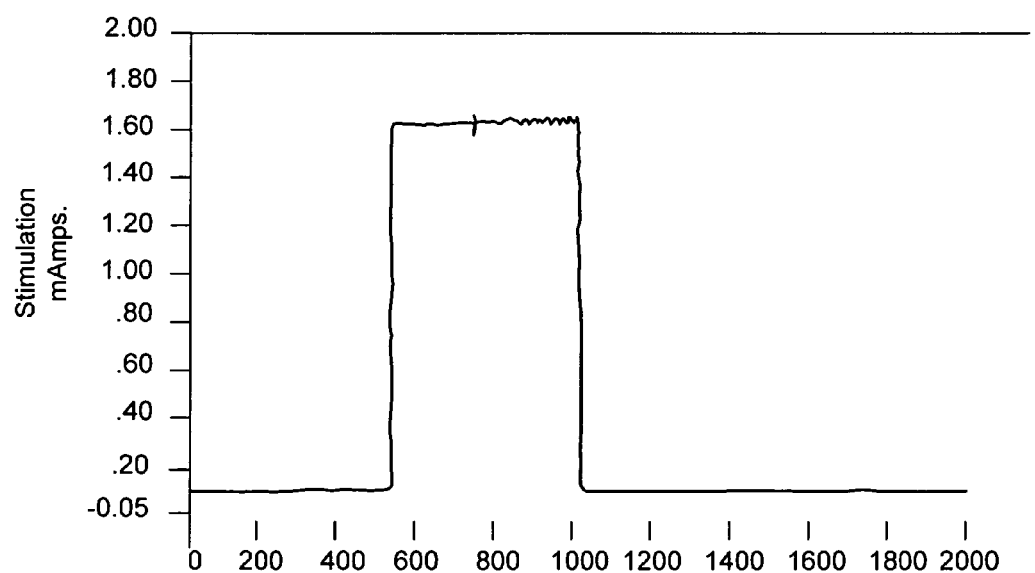
Figure 1B:
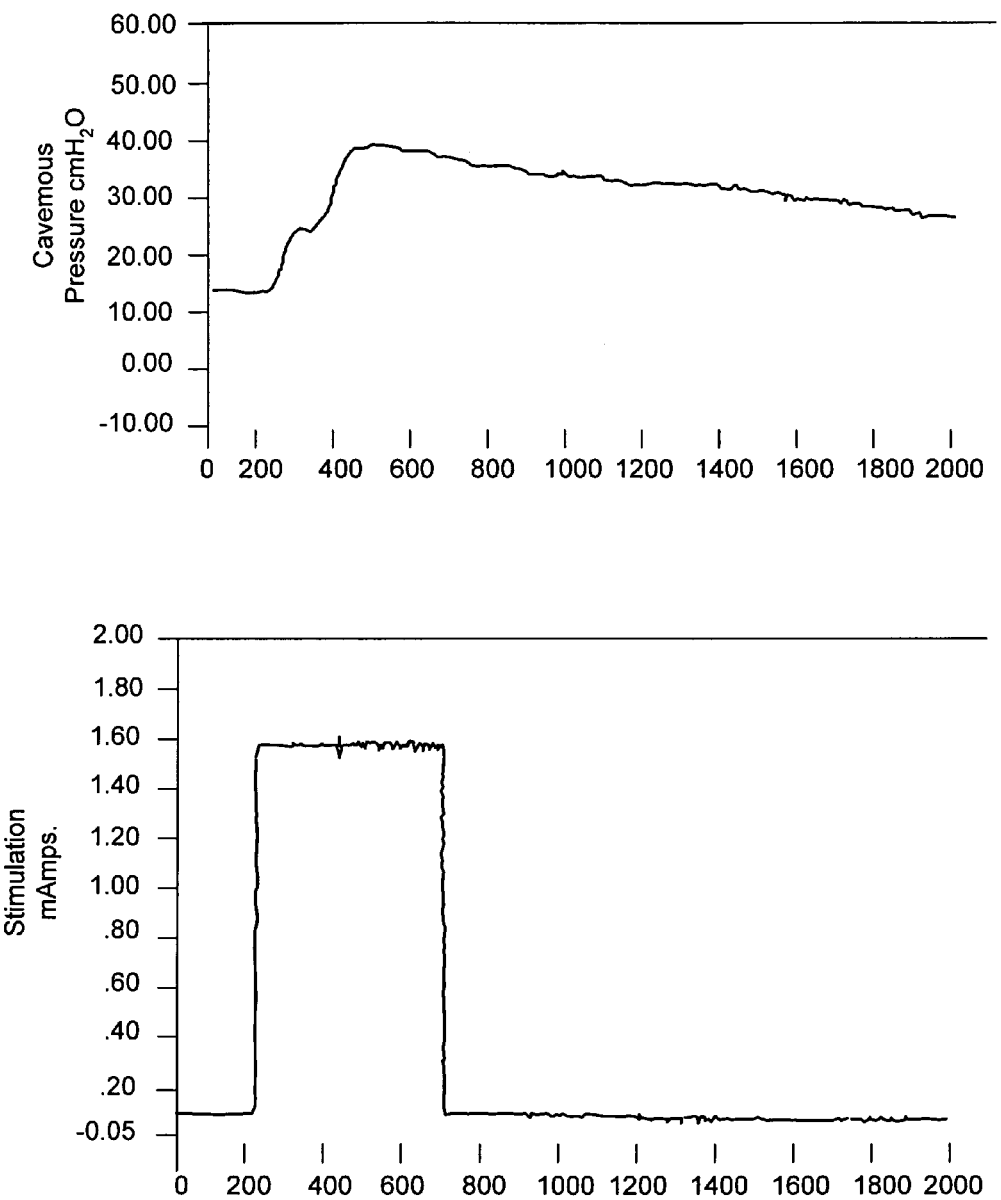
Figure 1C:
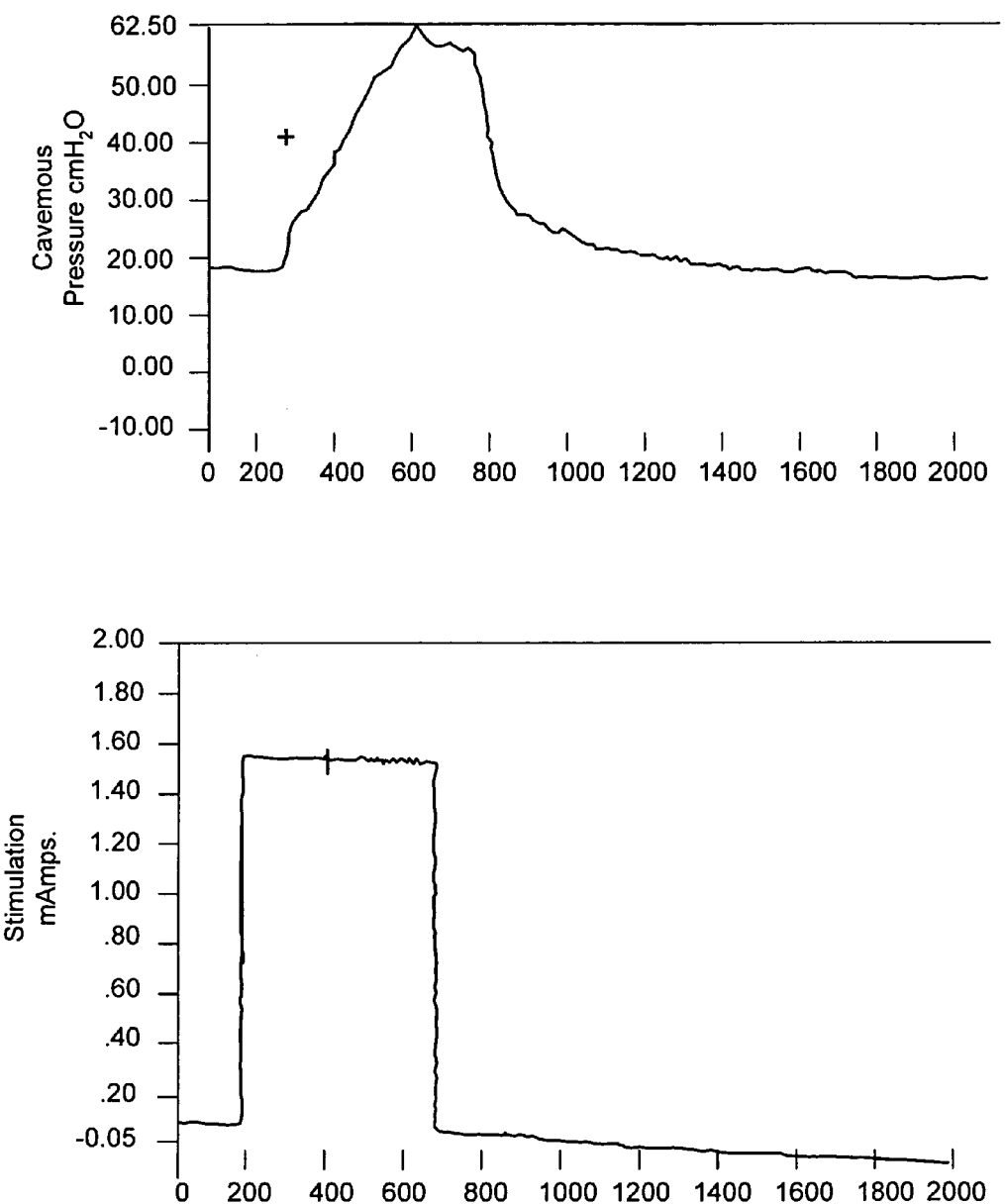

Unless defined otherwise, all technical and scientific terms used herein have the same meaning as is commonly understood by one of ordinary skill in the art to which this invention belongs. All patents, published patent applications and other publications and sequences from GenBank and other databases referred to herein are incorporated by reference in their entirety. If a definition set forth in this section is contrary to or otherwise inconsistent with a definition set forth in patents, published patent applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, an "erectile dysfunction (or impotence)" refers to the inability of a male mammal, e.g., a man, to achieve and maintain penile erection for satisfactory sexual intercourse.

As used herein, a "female sexual arousal disorder" refers to the persistent or recurring inability to attain or maintain adequate sexual excitement causing personal distress. It may be experienced as lack of subjective excitement or lack of genital (lubrication and swelling) or other somatic responses.

As used herein, "vascular endothelial growth factor (VEGF)" or "brain-derived neurotrophic factor (BDNF)" or "basic fibroblast growth factor (bFGF)" includes those variants with conservative amino acid substitutions that do not substantially alter their male erection stimulating activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p. 224).

As used herein, a "functional derivative or fragment of VEGF" refers to a derivative or fragment of VEGF that still substantially retains its function as an erection or sexual arousal stimulant. Normally, the derivative or fragment retains at least 50% of its erection or sexual function stimulating activity. Preferably, the derivative or fragment retains at least 60%, 70%, 80%, 90%, 95%, 99% and 100% of its erection or sexual function stimulating activity.

As used herein, an "agent that enhances production of VEGF" refers to a substance that increases transcription and/or translation of a VEGF gene, or a substance that increases post-translational modification and/or cellular trafficking of a VEGF precursor, or a substance that prolongs half-life of a VEGF protein.

As used herein, an "agent that enhances erection or female sexual arousal stimulating function activity of VEGF" refers to a substance that increases potency of VEGF's erection or sexual arousal stimulating activity, or a substance that increases sensitivity of a VEGF's natural ligand in an erection or sexual arousal stimulation signaling pathway, or a substance that decreases potency of a VEGF's antagonist.

As used herein, a "functional derivative or fragment of BDNF" refers to a derivative or fragment of BDNF that still substantially retains its function as an erection or female sexual arousal stimulant. Normally, the derivative or fragment retains at least 50% of its erection or female sexual arousal stimulating activity. Preferably, the derivative or fragment retains at least 60%, 70%, 80%, 90%, 95%, 99% and 100% of its erection or female sexual arousal stimulating activity.

As used herein, an "agent that enhances production of BDNF" refers to a substance that increases transcription and/or translation of a BDNF gene, or a substance that increases post-translational modification and/or cellular trafficking of a BDNF precursor, or a substance that prolongs half-life of a BDNF protein.

As used herein, an "agent that enhances erection or femal sexual arousal stimulating activity of BDNF" refers to a substance that increases potency of BDNF's erection or sexual arousal stimulating activity, or a substance that increases sensitivity of a BDNF's natural ligand in an erection or female sexual arousal stimulation signaling pathway, or a substance that decreases potency of a BDNF's antagonist.

As used herein, a "functional derivative or fragment of bFGF" refers to a derivative or fragment of bFGF that still substantially retains its function as an erection or female sexual arousal stimulant. Normally, the derivative or fragment retains at least 50% of its erection or female sexual arousal stimulating activity. Preferably, the derivative or fragment retains at least 60%, 70%, 80%, 90%, 95%, 99% and 100% of its erection or sexual arousal stimulating activity.

As used herein, an "agent that enhances production of bFGF" refers to a substance that increases transcription and or translation of a bFGF gene, or a substance that increases post-translational modification and/or cellular trafficking of a bFGF precursor, or a substance that prolongs half-life of a bFGF protein.

As used herein, an "agent that enhances erection or female sexual arousal function stimulating activity of bFGF" refers to a substance that increases potency of bFGF's erection or female sexual arousal stimulating activity, or a substance that increases sensitivity of a bFGF's natural ligand in an erection or female sexual arousal stimulation signaling pathway, or a substance that decreases potency of a bFGF's antagonist.

As used herein, a "combination" refers to any association between two or among more items.

As used herein, a "composition" refers to a any mixture of two or more products or compounds. It may be a solution, a suspension, liquid, powder, a paste, aqueous, non-aqueous or any combination thereof.

As used herein, a "nerve dysfunction" refers to the inability of the penis to hold the blood during erection or the persistent or recurring inability to attain or maintain adequate sexual excitement causing personal distress including, but not limited to dysfunction casued by diabetes mellitus, hypertension, hyperlipidemia, penile injury, aging, pelvic surgery or irradiation.

As used herein, an "arterial insufficiency" refers to reduced perfusion pressure and arterial flow associated with trauma or disease including, but not limited to, that associated with hypertension, hyperlipidemia, cigarette smoking, diabetes mellitus, and pelvic irradiation.

As used herein, a "venous leakage" refers to the inability of the penis to hold the blood during erection including, but not limited to diabetes mellitus, hypertension, hyperlipidemia, penile injury, aging, pelvic surgery or irradiation.

As used herein, a "hormonal insufficiency" refers to a group comprising, but not limited to, perimenopausal, post menopausal, cancer-related, hypogonadism, and osteoporosis.

As used herein, a "drug use" includes pharmaceutical drug use and substance abuse.

As used herein, a "surgery" refers to the performance of an operation including reconstructive, cosmetic, and restorative procedures and removal of an organ or tissue or some portion thereof.

As used herein, a "radiation" refers to treatment by photons, electrons, neutrons or other ionizing radiation.

As used herein, a "chemotherapy" refers to the administration of any agent that mediates the regression of malignant growth by inducing cell death or retarding cell growth through DNA damaging and non-DNA damaging mechanisms.

For clarity of disclosure, and not by way of limitation, the detailed description of the invention is divided into the subsections that follow. The following example is included for illustrative purposes only and is not intended to limit the scope of the invention.

B. Method to Prevent or Treat Male Erectile Dysfunction or Female Sexual Arousal Disorder.

In one aspect, the present invention provides a method for preventing or treating male erectile dysfunction or female sexual arousal disorder, which method comprises administering to a mammal to whom such prevention or treatment is needed or desirable, an effective amount of a) vascular endothelial growth factor (VEGF) or a functional derivative or fragment thereof, or a nucleic acid encoding said VEGF or functional derivative or fragment thereof, or an agent that enhances production and/or said male erection or female sexual arousal stimulating function of said VEGF; or b) brain-derived neurotrophic factor (BDNF) or a functional derivative or fragment thereof, or a nucleic acid encoding said BDNF or functional derivative or fragment thereof, or an agent that enhances production and/or said male erection or female sexual arousal stimulating function of said BDNF; or c) basic fibroblast growth factor (bFGF) or a functional derivative or fragment thereof, or a nucleic acid encoding said bFGF or functional derivative or fragment thereof, or an agent that enhances production and/or said male erection or female sexual arousal stimulating function of said bFGF, thereby preventing or treating said male erectile dysfunction or female sexual arousal disorder in said mammal.

Male erectile dysfunction or female sexual arousal disorder in any mammal can be treated or prevented by the present method. Preferably, male erectile dysfunction or female sexual arousal disorder in humans are treated or prevented. When human patients are treated, any suitable VEGF protein, or a functional derivative or fragment thereof, or any suitable VEGF nucleic acid, or a functional derivative or fragment thereof, can be used. Preferably, VEGF protein, or a functional derivative or fragment thereof, or VEGF nucleic acid, or a functional derivative or fragment thereof, is of human origin. But, suitable VEGF protein, or a functional derivative or fragment thereof, or VEGF nucleic acid, or a functional derivative or fragment thereof, of non-human origin can also be used when the non-human VEGF binds and stimulates the cell through the human VEGF receptor through cross-reactivity.

When human patients are treated, any suitable BDNF protein, or a functional derivative or fragment thereof, or any suitable BDNF nucleic acid, or a functional derivative or fragment thereof, can be used. Preferably, BDNF protein, or a functional derivative or fragment thereof, or BDNF nucleic acid, or a functional derivative or fragment thereof, is of human origin. But, suitable BDNF protein, or a functional derivative or fragment thereof, or BDNF nucleic acid, or a functional derivative or fragment thereof, of non-human origin can also be used when the non-human BDNF binds and stimulates the cell through the human BDNF receptor through cross-reactivity.

When human patients are treated, any suitable bFGF protein, or a functional derivative or fragment thereof, or any suitable bFGF nucleic acid, or a functional derivative or fragment thereof, can be used. Preferably, bFGF protein, or a functional derivative or fragment thereof, or bFGF nucleic acid, or a functional derivative or fragment thereof, is of human origin. But, suitable bFGF protein, or a functional derivative or fragment thereof, or bFGF nucleic acid, or a functional derivative or fragment thereof, of non-human origin can also be used when the non-human bFGF binds and stimulates the cell through the human bFGF receptor through cross-reactivity.

Any suitable DNA construct encoding VEGF, BDNF, or bFGF could be used in the present invention. Such constructs include, but are not limited to VEGF-Genbank accession number M32977, BDNF-Genbank accession number M61176, and bFGF-Genbank accession number E02544. Further contemplated for use in the present invention are the DNA sequences and resultant proteins described in U.S. Pat. Nos. 5,607,918, 5,438,121, 5,229,500, 5,180,820, 5,387,673, 5,155,214, and 5,026,839.

Any suitable method for the production or the stabilization of the VEGF, BDNF, or bFGF protein known to a skilled artisan may be used in this invention. Formulations that may be used in these inventions include, but are not limited to those described in U.S. Pat. Nos. 5,217,954, 5,235,043, 5,986,070, 6,077,829, 5,130,418, and 5,188,943.

The present invention provides a method for the treatment or prevention of male erectile dysfunction induced by or secondary to nerve dysfunction, arterial insufficiency, venous leakage, hormonal insufficiency, drug use, surgery, chemotherapy or radiation. In another aspect, the present invention provides a method for the treatment and prevention of female sexual arousal disorder induced by or secondary to nerve dysfunction, arterial insufficiency, hormonal insufficiency, drug use, surgery, chemotherapy or radiation.

In one preferred embodiment, the present invention provides a method for the treatment of female sexual arousal disorder by administering a) VEGF or a functional derivative or fragment thereof, or a nucleic acid encoding said VEGF or functional derivative or fragment thereof, or an agent that enhances production and/or said female sexual arousal stimulating function of said VEGF; or b) BDNF or a functional derivative or fragment thereof, or a nucleic acid encoding said BDNF or functional derivative or fragment thereof, or an agent that enhances production and/or said female sexual arousal stimulating function of said BDNF, or c) bFGF or a functional derivative or fragment thereof, or a nucleic acid encoding said bFGF or functional derivative or fragment thereof, or an agent that enhances production and/or said female sexual arousal stimulating function of said bFGF, in an amount sufficient to improve blood flow and regenerate nerve and smooth muscle in the clitoris and vaginal wall. A preferred route of administration is topically in a cream or via injection to the clitoris and vaginal wall of the patient.

In another preferred embodiment, the present invention provides for the treatment or prevention of male erectile dysfunction or female sexual arousal disorder by administering a) VEGF or a functional derivative or fragment thereof, or a nucleic acid encoding said VEGF or functional derivative or fragment thereof, or an agent that enhances production and/or said male erection or female sexual arousal stimulating function of said VEGF; or b)BDNF or a functional derivative or fragment thereof, or a nucleic acid encoding said BDNF or functional derivative or fragment thereof, or an agent that enhances production and/or said male erection or female sexual arousal stimulating function of said BDNF; or c) bFGF or a functional derivative or fragment thereof, or a nucleic acid encoding said bFGF or functional derivative or fragment thereof, or an agent that enhances production and/or said male erection or female sexual arousal stimulating function of said bFGF by intracavernous injection.

C. Combinations and Kits

In another aspect, the present invention provides for combination for preventing or treating male erectile dysfunction or female sexual arousal disorder, which combination comprises: a) an effective amount of an agent that stimulates male erection or female sexual arousal function; and b) one or more of the following: i) an effective amount of VEGF or a functional derivative or fragment thereof, or a nucleic acid encoding said VEGF or functional derivative or fragment thereof, or an agent that enhances the production and/or said male erection or female sexual arousal function stimulating function of said VEGF; ii) an effective amount of BDNF or a functional derivative or fragment thereof, or a nucleic acid encoding said BDNF or functional derivative or fragment thereof, or an agent that enhances production and/or said male erection or female sexual arousal function stimulating function of said BDNF; or iii) an effective amount of bFGF or a functional derivative or fragment thereof, or a nucleic acid encoding said bFGF or functional derivative or fragment thereof, or an agent that enhances production and/or said male erection or female sexual arousal function stimulating function of said bFGF.

In one embodiment, VEGF would be coadministered with bFGF or BDNF or both. Similarly, BDNF would be co-administered with bFGF or VEGF or both as would bFGF with VEGF or BDNF or both. The instant invention may further comprise the coadministration of an agent that enhances, complements, or is synergistic with the erectile stimulating or female sexual arousal stimulating activity of VEGF, BDNF, bFGF or some combination thereof. The agent may comprise an agent with independent pharmacologic activity or one that prolongs the functional or structural half-life of VEGF, BDNF, bFGF or some combination thereof. This invention also contemplates the administration of such VEGF, BDNF, bFGF, a combination thereof, with or without an accompanying agent simultaneously or separately to maximize the male erectile or female sexual arousal stimulating activity.

In a further embodiment of the invention, the VEGF, BDNF, bFGF or some combination thereof may be delivered to said mammal using a gene therapy vector. The exemplary vectors include, but are not limited to retroviruses, adenoviruses, adeno-associated viruses, lentiviruses, herpesviruses, and vaccinia viruses vectors. Replication-defective recombinant adenoviral vectors can be produced in accordance with known techniques. See, Quantin, et al., Proc. Natl. Acad. Sci. USA, 89:2581-2584 (1992); Stratford-Perricadet, et al., J. Clin. Invest., 90:626-630 (1992); and Rosenfeld, et al., Cell, 68:143-155 (1992).

The vector may include an expression construct of VEGF, BDNF, or bFGF nucleic acid, a functional derivative fragment thereof under the transcription control of a promoter. In a preferred embodiment, the gene therapy vector may be administered by intracaveronous injection of about 0.5 to 2 ml of AAV-VEGF, AAV-BDNF, or AAV-bFGF at a concentration of about $10^{10}$ virus titer. An example of a suitable promoter that may be used is the 763-base-pair cytomegalovirus (CMV) promoter. Viral promoters, cellular promoters/enhancers and inducible promoters/enhancers that could be used in combination with the nucleic acid contemplated for use in this invention include those listed in Jin, et al., U.S. Pat. No. 6,251,871. The expression construct may be inserted into a vector, such as pUC118, pBR322, or other known plasmid vectors, that includes an origin of replication. See, for example, Current Protocols in Molecular Biology, Ausubel, et al. eds., John Wiley & Sons, Inc. (2000), Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely effect the metabolism of the organism being treated.

The preferred embodiment of the VEGF, BDNF, bFGF or agent nucleic acid may be delivered via a adeno-associated viral (AAV) vector. These viruses are single-stranded DNA, nonautotomous parvoviruses that are able to integrate efficiently into the genome of nondividing cells of a very broad host range. Although ubiquitous in nature, AAV has not been shown to be associated with any known human disease and does not elicit an immune response in an infected human host. GOODMAN & GILMAN, PHARMACOLOGICAL BASIS OF THERAPEUTICS, 9th ed., McGraw-Hill Press (1996), p. 77-101. The method to produce purified replication deficient recombinant adeno-associated virions is described in Dwarki, et al., U.S. Pat. No. 6,221,646 B1, and its contents are incorporated in their entirety herein.

The present invention contemplates the use of AAV vectors that are known to those of skill in the art. For example, the vectors and vector production methods described in U.S. Pat. Nos. 5,589,377; 5,753,500; and 5,693,531. Another embodiment of this invention, the nucleic acid may be delivered in a retroviral vector, using vector and production method known in the art. See, for example, U.S. Pat. No. 5,830,725. A further embodiment would deliver the nucleic acid in an adenovirus vector, using vectors and vector production methods known in the art. See, for example, U.S. Pat. Nos. 6,063,622; 6,083, 750; 5,994,128; and 5,981,225.

In a further embodiment of the invention, the nucleic acid may be delivered in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). For a review of the procedures for liposome preparation, targeting and delivery of contents, see Mannino and Gould-Fogerite, *Bio Techniques,* 6:682 (1988). See also, Current Protocols in Molecular Biology, Ausubel, et al. eds., John Wiley & Sons Press (2000), Chapters 9 and 16. The process of making and loading the liposomes with nucleic acid or protein may employ techniques known in the art. See, for example, U.S. Pat. Nos., 6,007,838; 6,197,333 B1; 6,133,026; 6,120,798; 5,939,096; 5,662,931; 5,552,157; and 5,270,053.

According to the present invention, the VEGF, BDNF, or bFGF peptides, proteins, polynucleotides, nucleic acids, or agent that enhances production and/or erection or sexual arousal stimulating function of said factor may be formulated for intracavernous injection, subcutaneous injection, intravenous injection, intramuscular injection, intradermal injection, or topical administration. The method may employ formulations for injectable administration in unit dosage form, in ampules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

Pharmaceutically acceptable compositions and methods for their administration that may be employ for use in this invention include, but are not limited to those described in U.S. Pat. Nos. 5,736,154; 6,197,801 B1; 5,741,511; 5,886,039; 5,941,868; 6,258,374 B1; and 5,686,102.

One preferred embodiment is the intracavernous administration of about 0.5 to 2.0 ml of the AAV-VEGF, AAV-BDNF, or AAV-bFGF gene therapy vector at a concentration of about $10^{10}$ virus titer.

The magnitude of a therapeutic dose in the acute or chronic treatment of erectile dysfunction or female sexual arousal disorder will vary with the severity of the condition to be treated and the route of administration. The dose, and perhaps dose frequency, will also vary according to age, body weight, condition and response of the individual patient. A preferred dosage for the treatment or prevention of male erectile dysfunction and/or female sexual arousal disorder is about 10-200 mcg/70 Kg body about once every two to six months.

One preferred embodiment of the present invention contemplates the administration by the application of a cream or by an injection to the clitoris and vaginal wall of a patient with female sexual arousal disorder in an amount sufficient to improve blood flow and regenerate nerve and smooth muscle in the clitoris and vaginal wall.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, VEGF, BDNF, or bFGF peptides, proteins, polynucleotides, nucleic acids, or agent that enhances production and/or erection or sexual arousal stimulating function of said factor may be combined as the active in intimate admixture with a pharmaceutical carrier or incipient according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of VEGF, BDNF, or bFGF to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the VEGF, BDNF, bFGF, an agent stimulating the production and/or function of VEGF, BDNF, bFGF, or some combination thereof in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

D. EXAMPLES

Example 1

The Effect of Vascular Endothelial Growth Factor (VEGF) on a Rat Model of Traumatic Arteriogenic Erectile Dysfunction Animal model. The experimental protocols and animal care were approved by our institutional Committee on Animal Research. Fifty 3-months-old male Sprague Dowley rats weighing 350~400 gm. were anesthetized with intraperitoneal pentobarbital (35 mg/kg) after being sedated with inhalation of methoxyflurane. Midline laparotomy was performed to identify the iliac vessels. Under operating microscope, the iliac veins were carefully dissected to expose the internal iliac arteries that vary from 2 to 4 in number. Rats in the experimental group (n=44) underwent bilateral ligation of internal iliac arteries at their origin. A separate incision was made in the perineum to identify one of the crura. A 23-gauge scalp vein needle was inserted to the crus and connected to a pressure monitor for intracavernous pressure monitoring during electrostimulation of the cavernous nerve. Additional ligation of arterial branches was performed until minimal or no intracavernous pressure rise during electrostimulation. Intracavernous injection of 4 μg of VEGF in PBS (phosphate-buffered saline) with 0.1% BSA (bovine serum albumin); 2 μg of VEGF in PBS with 0.1% BSA; or PBS solution with 0.1% BSA was then administered through the same needle to 3 groups of rats (n=16, 12 and 16 respectively). The wound was closed in layers and the animals were closely monitored for up to 6 weeks. At week 1, 2 and 6 roughly one-third of rats from each group underwent electrostimulation of the cavernous nerve to assess erectile function and then sacrificed.

Penile tissues of 3 rats randomly chosen from each of the three subgroups at 2 and 6 weeks were obtained for immunohistochemical staining and electron microscopic examination.

Electrical stimulation. Bipolar platinum-wire electrodes were used to stimulate the cavernous nerve. The exposed end of the electrodes were hooked around the nerve to be stimulated, with the positive electrode being positioned proximally and the negative electrode two to three mm distally. Stimulus parameters were 1.5 volts, frequency of 20 pulses per second, pulse width of 0.2 msec, and the duration of 50 seconds. Intracavernous pressure was monitored and recorded by inserting a number 23 scalp vein needle to one of the crura and connected to a pressure monitor.

Immunohistochemical Staining. Penile tissue were fixed for 3 hours in a cold, freshly prepared solution of 2% formaldehyde, 0.002% picric acid in 0.1 M. phosphate buffer, pH 8.0. Tissues were cryoprotected for 24 hours in cold 30% sucrose in 0.1 M. phosphate buffer, pH 8.0. They were then embedded in O.C.T. compound (Tissue-Tek, Miles Laboratory), frozen in liquid nitrogen, and stored at −70° C. After freezing, Cryostat tissue sections were cut at 10 μm., adhered to charged slides, air-dried, and hydrated for 5 min. with 0.05 M. sodium phosphate buffer (PBS, pH 7.4). Sections were treated with hydrogen peroxide/methanol to quench endogenous peroxidase activity. After rinsing with water, sections were washed twice in PBS for 5 min. followed by 30 min. of room-temperature incubation with 3% horse serum/PBS/0.3% triton X-100. After draining solution from sections, tissues were incubated for 60 min. at room temperature with mouse monoclonal anti-nNOS (Transduction Laboratories, Lexington, Ky.) at a 1:500 dilution. After washing for 5 min. with PBS/TX and then for 5 min. twice with PBS alone, sections were immunostained with the avidin-biotin-peroxidase method (Elite ABC, Vector Labs, Burlingame Calif.), with diaminobenzidine as the chromogen, followed by counterstaining with hematoxylin.

Electron Microscopy. The penis was dissected, thinly sliced (~1 mm thick) and placed in Karnovsky's fixative (1% para-formaldehyde/3% glutaraldehyde/0.1 M sodium cacodylate buffer, pH 7.4) at room temperature for 30 minutes and then stored at 4° C. The fixed tissue was then rinsed in buffer, post-fixed in 2% aqueous OsO4, and stained en bloc with uranyl acetate before being dehydrated in ethanol, cleared in propyline oxide, and embedded in eponatel 12 (Ted Pella Co., Redding, Ca.). Thick sections were cut and stained with toludine blue, examined under light microscope to select the area to be thin-sectioned. Thin sections were cut by Leica ultracut E microtome (Bannockburn, Ill.), stained with uranyl acetate and Reynold's Lead to enhance contrast and examined under Philips Tecnai 10 electron microscope (Eidhoven, Netherland).

Statistics. Data were evaluated with Mann-Whitney ranksum test. Significance was defined as $p<0.05$.

Erectile function. The peak sustained intracavernous pressure during electrostimulation of the cavernous nerve is shown in Table I. There is no difference in intracavernous pressure between the sham operated and the normal rats. After bilateral ligation of the internal iliac arteries, the intracavernous pressure immediately dropped to around 20 cm $H_2O$ and produced no or minimal pressure increase in response to neurostimulation in all rats. In the PBS-treated group, poor erectile response persisted at weeks 1 and 2 and slight recovery of erectile function was noted at week 6.

In the VEGF-treated rats, at weeks 1 and 2, moderate recovery of erectile function was noted in the 4-μg group but not the 2-μg group. At week 6, statistically significant improvement in intracavernous pressure was seen in both the 2-μg and 4-μg groups as compared with the PBS-treated group. The intracavernous pressure of the 4-μg group was also significantly higher than that of the 2-μg group.

To identify the new source of blood flow in the 4-μg VEGF-treated group, we noted a decrease in erectile response after clamping one external iliac artery and no erectile response at all after clamping both external iliac arteries. This strongly suggests that the collateral vessels were derived from the external iliac arteries.

TABLE 1

Peak sustained intracavernous pressure (cm $H_2O$) during electrostimulation of the cavernous nerves in saline- and VEGF-treated rats

| | Saline treated Group | VEGF-treated Group | |
|---|---|---|---|
| | PBS + 0.1% BSA | PBS + 2 μg VEGF | PBS + 4 μg VEGF |
| Week 1 | 20.33 ± 3.45 (n = 6) | 23.50 ± 2.38 (n = 4) | 71.17 ± 16.89 (n = 6) |
| Week 2 | 27.75 ± 9.70 (n = 4) | 43.00 ± 8.37 (n = 4) | 86.25 ± 8.18 (n = 4) |
| Week 6 | 46.75 ± 14.85 (n = 6) | 69.00 ± 8.83 (n = 4) | 96.67 ± 13.50 (n = 6) |

Sham operated group (n = 6): 98 ± 8.50

Histochemistry

There was a trend of decreased nNOS-immunoreactive in both dorsal and intracavernous nerves two weeks after arterial ligation in all subgroups. At week 6, moderate recovery of nNOS-positive nerve fibers was noted in both dorsal and intracavernous nerves in both 2 & 4 μg VEGF-treated groups but not in the PBS-treated group. However, the differences were not statistically significant by computer-assisted image analysis.

Electron Microscopy:

Dorsal nerve: In sham-operated rats, no difference was noted between specimens obtained from the 2 and 6-week groups. The dorsal nerve in these rats was filled with both myelinated and non-myelinated nerve bundles. The mean diameter of the individual myelinated nerve axon was 4.42±1.36 μm (excluding myelin sheath). The mean thickness of the myelin sheath was 0.58+0.21 μm. The mean diameter of the non-myelinated nerve fibers was 0.96±0.37 μm. The nuclei of Schwann cells were seen occasionally near the nerve fibers.

In ligated+PBS treated rats, dramatic changes were noted at week 2. There was an increase in the number of Schwann cells and many of which contained vacuous within the cytoplasm. There was also a decrease in the number of both non-myelinated and myelinated nerve fibers. Overall the size of the axons was smaller than that of the controls, and many of the non-myelinated nerve fibers were smaller and less discrete. At week 6, varying degree of regeneration of both myelinated and non-myelinated nerve fibers was apparent. However, the nerve fibers of both the myelinated and non-myelinated nerve fibers were still smaller than the control groups. (mean myelinated axon 3.17±1.01 μm, myelin sheath 0.46±0.11 μm, non-myelinated axon 0.81±0.38 μm, p=0.062, 0.189, and 0.069 respectively compared with those of the sham group.) Many of the non-myelinated fibers were less than one third of the size of the larger ones. There was also an increase in the number of nucleated Schwann cells.

At week 6, in ligated rats treated with 4 μg of VEGF, the mean diameter of the myelinated axons (6.19±0.38 μm) was larger than the ligated+PBS treated ones (3.17±1.01 µm) with a p=0.008. The mean diameter of the nonmyelinated axons was 0.82±0.45 µm which was similar to that of the ligated+ PBS treated rats (0.81±0.38 µm). However, the non-myelinated nerve fibers appeared more even in size.

Intracavernosal smooth muscle: In sham-operated rats, no difference was noted between the specimens from the 2 and 6-week groups. The smooth muscle cells, most of which were arranged in clusters, were embedded in fine strands of fibroconnective tissue. The cytoplasm of these myocytes contained abundant contractile myofilaments and dense bodies. Occasionally, small aggregates of organelles, including mitochondria, rough endoplasmic reticulum and Golgi apparatus, were found adjacent to the nucleus. The cell membrane (sarcolemma) was consisted of many alternating dense and light bands with the latter containing numerous pinocytotic vesicles (caveolae). The intercellular spaces were narrow and many cell-cell contacts (gap junctions) were visible. Nerve terminal varicosities were seen occasionally near clusters of smooth muscle cells.

At week 2, in ligated+PBS-treated rats, many atrophic smooth muscle cells separated by large amounts of collagen fibers were noted. These atrophic smooth muscle cells appeared scattered in a sheet of connective tissues while normal smooth muscle cells were separated only by minimal amounts of connective tissues. At week 6, the number of normal-appearing smooth muscle cells increased, although many of them still showed significant loss of myofilaments.

In ligated+4 µg of VEGF-treated rats (both 2 and 6-week groups), most of the smooth muscle cells appeared normal with large amount of myofilaments and narrow intercellular spaces.

Endothelium: In sham-operated rats, the cavernous sinusoids were lined with intact endothelium, the cytoplasm of which contained numerous pinocytotic vesicles (caveolae), mitochondria, rough endoplasmic reticulum, and Golgi apparatus. The nuclei of the endothelial cells were sparsely seen and appeared flattened. In ligated+PBS-treated rats, (both 2 and 6-week groups) the capillary and cavernous sinusoidal endothelium appeared normal, although increase in the number of endothelial cells could be seen in some fields. In ligated+4 µg of VEGF-treated rats, (both 2 and 6-week groups) striking differences were noted when compared with other groups of rats. Many reactive endothelial cells with plump nuclei could be seen lining the sinusoids and capillaries. These endothelial cells were larger and more numerous indicative of endothelial cell hypertrophy and hyperplasia.

References For Example 1

1. Goldstein, I., et al., Radiation-associated impotence. A clinical study of its mechanism. Jama, 1984. 251(7): p. 903-10.
2. Rosen, M. P., et al., *Arteriogenic impotence: findings in 195 impotent men examined with selective internal pudendal angiography. Young Investigator's Award.* Radiology, 1990. 174(3 Pt 2): p. 1043-8.
3. Levine, F. J., A. J. Greenfield, and I. Goldstein, *Arteriographically determined occlusive disease within the hypogastric-cavernous bed in impotent patients following blunt perineal and pelvic trauma.* Journal of Urology, 1990. 144(5): p. 1147-53.
4. Heaton, J. P., et al., *Coronary artery bypass graft surgery and its impact on erectile function: a preliminary retrospective study.* International Journal of Impotence Research, 1996. 8(1): p. 35-9.
5. D'Amore, P. A. and R. W. Thompson, *Mechanisms of angiogenesis.* Annual Review of Physiology, 1987. 49(9-10): p. 453-64.
6. Folkman, J., C. C. Haudenschild, and B. R. Zetter, *Long-term culture of capillary endothelial cells.* Proceedings of the National Academy of Sciences of the United States of America, 1979. 76(10): p. 5217-21.
7. Gross, J. L., D. Moscatelli, and D. B. Rifkin, *Increased capillary endothelial cell protease activity in response to angiogenic stimuli in vitro.* Proceedings of the National Academy of Sciences of the United States of America, 1983. 80(9): p. 2623-7.
8. Leung, D. W., et al., *Vascular endothelial growth factor is a secreted angiogenic mitogen.* Science, 1989. 246(4935): p. 1306-9.
9. Poltorak, Z., et al., *VEGF145, a secreted vascular endothelial growth factor isoform that binds to extracellular matrix.* Journal of Biological Chemistry, 1997. 272(11): p. 7151-8.
10. Hopkins, S. P., et al., *Controlled delivery of vascular endothelial growth factor promotes neovascularization and maintains limb function in a rabbit model of ischemia.* Journal of Vascular Surgery, 1998. 27(5): p. 886-94; discussion 895.
11. Asahara, T., et al., *Local delivery of vascular endothelial growth factor accelerates reendothelialization and attenuates intimal hyperplasia in balloon-injured rat carotid artery [see comments].* Circulation, 1995. 91(11): p. 2793-801.
12. Hariawala, M. D., et al., *VEGF improves myocardial blood flow but produces EDRF-mediated hypotension in porcine hearts.* Journal of Surgical Research, 1996. 63(1): p. 77-82.
13. Bauters, C., et al., *Recovery of disturbed endothelium-dependent flow in the collateral-perfused rabbit ischemic hindlimb after administration of vascular endothelial growth factor [see comments].* Circulation, 1995. 91(11): p. 2802-9.
14. Bauters, C., et al., *Physiological assessment of augmented vascularity induced by VEGF in ischemic rabbit hindlimb.* American Journal of Physiology, 1994. 267(4 Pt 2): p. H1263-71.
15. Takeshita, S., et al., *Therapeutic angiogenesis. A single intraarterial bolus of vascular endothelial growth factor augments revascularization in a rabbit ischemic hind limb model.* Journal of Clinical Investigation, 1994. 93(2): p. 662-70.
16. Takeshita, S., et al., *Intramuscular administration of vascular endothelial growth factor induces dose-dependent collateral artery augmentation in a rabbit model of chronic limb ischemia.* Circulation, 1994. 90(5 Pt 2): p. 11228-34.
17. Takeshita, S., et al., *Time course of increased cellular proliferation in collateral arteries after administration of vascular endothelial growth factor in a rabbit model of lower limb vascular insufficiency.* American Journal of Pathology, 1995. 147(6): p. 1649-60.
18. Banai, S., et al., *Angiogenic-induced enhancement of collateral blood flow to ischemic myocardium by vascular endothelial growth factor in dogs.* Circulation, 1994. 89(5): p. 2183-9.
19. Baumgartner, I., et al., *Constitutive expression of phVEGF165 after intramuscular gene transfer promotes collateral vessel development in patients with critical limb ischemia [see comments].* Circulation, 1998. 97(12): p. 1114-23.

20. Losordo, D. W., P. R. Vale, and J. M. Isner, *Gene therapy for myocardial angiogenesis.* American Heart Journal, 1999. 138(2 Pt 2): p. 132-41.
21. Azadzoi, K. M. and I. Saenz de Tejada, *Hypercholesterolemia impairs endothelium-dependent relaxation of rabbit corpus cavernosum smooth muscle.* Journal of Urology, 1991. 146(1): p. 238-40.
22. Kim, J. H., et al., *Experimental hypercholesterolemia in rabbits induces cavernosal atherosclerosis with endothelial and smooth muscle cell dysfunction.* Journal of Urology, 1994. 151(1): p. 198-205.
23. Neufeld, G., et al., *Vascular endothelial growth factor (VEGF) and its receptors.* Faseb Journal, 1999. 13(1): p. 9-22.
24. Liu, X*, Lin, C-S*, Graziottin, T, Resplande, J, and Lue, T F: Vascular Endothelial Growth Factor Promotes Proliferation and Migration of Cavernous Smooth Muscle Cells. J Urol., 2001. 166: 354-360.
25. Magovern, C. J., et al., *Regional angiogenesis induced in nonischemic tissue by an adenoviral vector expressing vascular endothelial growth factor.* Human Gene Therapy, 1997. 8(2): p. 215-27.
26. Folkman, J. and Y. Shing, *Angiogenesis.* Journal of Biological Chemistry, 1992.267(16): p. 10931-4.
27. Ferrara, N., *The role of vascular endothelial growth factor in pathological angiogenesis.* Breast Cancer Research and Treatment, 1995.36(2): p. 127-37.
28. Walder, C. E., et al., *Vascular endothelial growth factor augments muscle blood flow and function in a rabbit model of chronic hindlimb ischemia.* Journal of Cardiovascular Pharmacology, 1996.27(1): p. 91-8.
29. Harada, K., et al., *Vascular endothelial growth factor administration in chronic myocardial ischemia.* American Journal of Physiology, 1996. 270(5 Pt 2): p. H1791-802.
30. Dvorak, H. F., et al., *Vascular permeability factor/vascular endothelial growth factor and the significance of microvascular hyperpermeability in angiogenesis.* Current Topics in Microbiology and Immunology, 1999. 237(1): p. 97-132.
31. Houck, K. A., et al., *Dual regulation of vascular endothelial growth factor bioavailability by genetic and proteolytic mechanisms.* J. Biol. Chem., 1992. 267(36): p. 26031-7.

Example 2

Intracavernosal Vascular Endothelial Growth Factor (VEGF) and Adenoassociated virus mediated VEGF Gene Therapy Prevents and Reverses Venogenic Erectile Dysfunction in Rats Animal groups: Male Sprague-Dawley rats age 3-6 months (wt 350-450 grams) were used in this study. They were housed in our animal care facility with rat chow and water available ad libitum on a 12 hr light/dark cycle. All animal care, treatments and procedures were performed in compliance with requirements of the Committee on Animal Research at our institution. Rats were randomly divided for the animal model of vasculogenic ED (Experiment 1) and the VEGF prevention trial (Experiment 2). For the VEGF treatment trial (Experiment 3), the animals underwent castration and then were treated with VEGF after venous leak was demonstrated, to evaluate the efficacy of VEGF treatment in reversing established venogenic ED.

Experiment 1: To determine normal values for rodent pharmacologic cavernosometry and validate the model of venogenic ED in the rat, vasculogenic ED was induced. Arterial insufficiency was produced after performing a bilateral ligation of the internal iliac arteries. The acute and chronic effects of arterial insufficiency were evaluated 7 days and 30 days after bilateral iliac artery ligation (n=7). Venogenic ED was induced by castration, and pharmacologic cavernosometry was performed 6 weeks after surgery (n=10). Control animals underwent a sham laparotomy and studied 6 weeks later (n=13).

Experiment 2: For the prevention trial of VEGF in rats with venogenic erectile ED, adult males were castrated and immediately treated with hormone, intracavernosal VEGF. Hormone replacement was accomplished using a subcutaneously placed testosterone-filled silastic implant (n=6), as previously described[17]. A therapeutic testosterone serum titer was confirmed in this animal group by testosterone radioimunoassay performed by the biomedical core lab at our institution[18]. Intracavernous treatment with VEGF was administered using either recombinant VEGF protein (n=5) or an adeno-associated virus vector expressing the VEGF gene (AAV-VEGF, n=14). Control animals received an silastic implant containing saline (n=3), an intracavernous injection of normal saline (n=3) or an adenovirus transfection vector expressing lacZ reporter gene without the VEGF gene (AAV-LacZ, n=11).

Experiment 3: The trial of VEGF treatment was performed in castrated animals that were shown, 6-8 weeks following castration, to develop venogenic erectile ED by pharmacologic cavernosometry. These animals (n=8) were treated with intracavernous VEGF protein and then after one month cavernosometry repeated to measure the effect of VEGF treatment.

Animal Treatments:

Surgical preparation: Prior to all surgical procedures, animals received anesthesia consisting of isoflurane inhalation as pre-anesthetic followed by an intraperitoneal injection of sodium pentobarbital (40 mg/kg). After the animal was asleep, electric clippers were used to trim the ventral abdominal hair and the skin was prepped with clorhexidine scrub. Antiseptic technique was maintained for all procedures. Following surgery, the anterior abdominal fascia and skin were approximated with 4-0 silk suture, analgesic buprenorphine (0.5 mg/kg SC) was administered and the animal allowed to awaken covered with a heating pad. Euthanasia was accomplished by an intraperitoneal injection of sodium pentobarbital (200 mg/kg) followed by bilateral thoracotomy when the animal was fully asleep.

Arterial ligation surgery: A 2 cm midline longitudinal low abdominal incision was made and a wheatlander retractor placed so that the plane between the prostate and sigmoid colon could be bluntly opened. A dissecting microscope with 2.5-10× objectives was essential to safely performing this procedure. Using sterile cotton-tipped swabs, the iliac artery bifurcation was identified and the common iliac exposed to the external iliac take-off. The internal iliac arteries were identified as those medial branches off the common iliac between the iliac bifurcation and the take-off of the external iliac. These were doubly ligated using 7-0 nylon sutures. After this was performed on both the right and left side, the incision was closed and the animal recovered as noted above.

Castration: A 2 cm midline longitudinal low abdominal incision was made and each testicle was grasped using forceps and brought into the incision. Each gubernaculum was divided using electrocautery and then the spermatic cords ligated with 4-0 silk suture and divided. After confirming hemostasis, the abdomen was closed and the rat recovered as above.

Intracorporal injections: A 1.5 cm oblique incision was made in the lower abdominal skin extending from the midline just above the penile hilum to below the level of the glans about 1 cm lateral to the midline. The skin was sharply dissected from the anterior surface of the penis and then the penis was retracted anteriorly using a towel clamp placed around it atraumatically with the foreskin left intact. Using blunt dissection the penile base and crura were exposed. The ischiocavernosus muscles were sharply dissected off the anterior surface of the crus until the white of the tunica albuginea of the corpora cavernosa was identified. The crus was then gently cannulated using a 23 gage butterfly needle, and saline flush with a visual erectile response was used to confirm that the needle tip was truly intracavernosal. The intracavernosal injections were then administered with either VEGF protein (Calbiochem, La Jolla, Calif. #676472) at the dosage 4 ug/injection (in 0.1 cc PBS with 0.1% BSA), AAV-VEGF ($10^{10}$ viral particles in 0.1 cc NS), AAV-LacZ ($10^{10}$ viral particles in 0.1 cc NS), or 0.1 ml NS alone. The AAV-VEGF and AAV-LacZ constructs were a generous gift from Dr. Yuet W. Kan (Howard Hughes Medical Research Institute, San Francisco, Calif.) [19,20]. Following injection, the needle was left in place for 5 minutes and then removed to allow the medication to diffuse throughout the cavernosal space. Immediately thereafter, pinpoint electrocautery was applied to the needle hole for hemostasis and then the wound was closed and the animal recovered as above.

Testosterone replacement: Following castration, testosterone- or saline-filled silastic implants were placed in the subcutaneous tissue of the anterior abdominal wall, as previously described[17]. Implants were prepared using sterile silastic tubing (Dow Corning, Midland, Mich. #602-265, inner diameter 0.062") that was filled with testosterone propionate powder (Sigma Chemical, St. Louis, Mo.) with the aid of wall suction. By radioimmunoassay[18], serum testosterone titer was found to be undetectable in the castrated animals and in the normal range for animals given testosterone implants.

Pharmacologic cavernosometry in the rat: To perform pharmacologic cavernosometry, both the right and left crura were separately cannulated using 23 gauge butterfly needles as described above. One cannula was flushed with sterile heparinized saline (100 U heparin/ml NS) and attached to a pressure detector for continuous intracorporal pressure (ICP) monitoring as previously described[11]. The contralateral cannula was attached to an infusion pump (Harvard Pump, Southwick, Mass. #55-2222), filled with sterile dilute heparinized saline (20 U heparin/ml NS). The baseline ICP was recorded (flaccid ICP) and then a dose of papavarine (1 mg in 0.1 cc NS) was administered through the infusion cannula. Five minutes was allowed for the papavarine to diffuse throughout the corpora and then the infusion cannula was flushed with heparinized saline and the pressure monitor cannula vented to normalize ICP after flushing. After 5 minutes more, the ICP was again recorded (ICP after papavarine) and the infusion started. An infusion rate of 0.05 ml/min was started and increased (by 0.05 ml/min every 10 seconds) until the ICP started to rise. Subsequent increases in inflow rate were made only after the ICP reached a plateau pressure. By slowly adjusting the inflow rate, an intracorporal pressure of 100 cm $H_2O$ (erectile pressure) was reached and the infusion rate required to maintain this pressure recorded (the maintenance rate). After this pressure was steady for 20 seconds, the infusion was terminated and the change in ICP over the subsequent 60 seconds was recorded (the drop rate).

Tissue preparation: After pharmacologic cavernosometry was performed, the penis was amputated at the crural bony attachments and immediately placed in ice-cold saline. The Y-shaped crura was sharply cut from the penile base and then a 1 mm thick slice cut for electron microscopy and placed in Karnofsky's solution (3% gluteraldehyde, 1% para-formaldehyde, 0.1 M sodium cacodylate buffer, pH 7.4). A 3 mm thick section of the distal penile shaft was then cut and placed in 10% normal buffered formalin for paraffin sections, and the balance of the penile shaft was flash frozen using dry ice in OCT compound (Sakura Finetek USA, Torrance, Calif.) for frozen sectioning and immunohistochemistry.

Immunohistochemistry: Frozen sections were cut at 10 microns, adhered to charged slides, air dried for 15 minutes then rehydrated with 0.05M PBS for 5 minutes. Sections were treated with hydrogen peroxide/methanol to quench endogenous peroxidase activity. After rinsing, sections were washed twice in PBS for 5 minutes then incubated with 3% horse serum and 0.3% triton X-100 at room temperature for 30 minutes. The serum solution was drained and then sections were incubated for 60 minutes with mouse monoclonal anti-alpha-smooth muscle actin (Sigma, St. Louis, Mo.) at a dilution of 1:4000 in PBS. After washing, sections were immunostained using the avidin-biotin-peroxidase method (Elite ABC-Vector Labs, Burlingame, Calif.), with diaminobenzidine as the chromogen, followed by counterstaining with hematoxylin. Immunochemistry was performed in penile tissues from 4 rats randomly chosen from each subgroup.

Enzyme-linked immuno-sorbent assay: Serum samples from both systemic and penile blood were collected after whole-blood centrifugation. Solid phase enzyme-linked immuno-sorbent assay for VEGF was performed using the Quantikine M mouse VEGF Immunoassay Kit (R&D Systems, Minneapolis, Minn.) as previously described[21]. Briefly, samples were diluted and added to micro plate strip wells that were then treated with the enzyme-labeled immunoreactant VEGF conjugate. After incubation for 2 hours and washing, the substrate solution was added and incubated for 30 minutes. The stop solution was added and then the optical density in each well determined using a micro plate reader set to 450 nm. Sample results were plotted on a curve generated by the optical density of standard samples ranging in concentration (0-500 pg/ml VEGF).

Transmission electron microscopy: After fixing in Karnofsky's solution for 30 minutes at room temperature, 1 mm sections at the penile base were stored at 40 C until processed, as previously described 22. Briefly, samples were rinsed in PBS, post-fixed in 2% aqueous OsO4 and stained en bloc with uranyl acetate. They were then dehydrated in ethanol, cleared in propyline oxide and embedded in Eponate 12 (Ted Pella Co., Redding, Calif.). Thick sections were cut and stained with toluidine blue to select specific areas for thin sectioning. Thin sections were cut, stained with both uranyl acetate and Reynold's Lead, and examined under the Phillips Tecnai 10 transmission electron microscope. Penile tissues from 4 randomly chosen rats in each subgroups were subjected to electron microscopic examinations.

Statistical analysis: Data in the present studies was analyzed using the student's t-test (homoscedastic, 2-tailed) when 2 means were compared (Experiment 1 and 2). A paired, 2-tailed t-test was used where values represent findings before and after treatment in the same animals (Experiment 3).

Results

Experiment 1: Model validation: The first goal was to determine normal values for pharmacologic cavernosometry in a rat model of vasculogenic ED. As shown in Table 2, flaccid ICP were comparable, in the range of 30 cm H2O. After papavarine injection, however control animals had a steep rise in ICP to >100 cm $H_2O$ while the castrated and ligated animals had less response. Only a minimal increase in ICP (5-10 cm $H_2O$) was noted in the animals following either castration or chronic internal iliac ligation, characteristic of vasculogenic ED. Acute ligation animals had a better response to papavarine yet significantly less than seen in normal animals. After the infusion was started, both the control and acute ligation group promptly achieved erectile pressure with minimal inflow required. When the infusion was stopped, these animals had a minimal pressure drop, evidencing their intact veno-occlusive mechanism. The castration and chronic ligation groups, on the other hand, required a significantly higher infusion rate to maintain erectile pressure and experienced a steep pressure drop when the infusion was terminated. These findings are characteristic of venous leakage in the chronic ligation and castration groups.

TABLE 2

(Experiment 1) Cavernosometric findings in rat model of vasculogenic ED.

|  | Flaccid ICP (cm $H_2O$) | ICP After Papavarine (cm $H_2O$)* | Maintenance Rate (ml/min)* | Drop Rate in 1 min. (cm $H_2O$)* |
| --- | --- | --- | --- | --- |
| Control | 35.4(+/−9.3) | 104(+/−59) | 0.024(+/−0.3) | 9(+/−13) |
| Castration | 22.0(+/−5.2) | 35.0(+/−5.0) | 1.14(+/−0.5) | 75(+/−5.4) |
| Acute Ligation | 28.7(+/−7.6) | 73.3(+/−10) | 0.06(+/−0.12) | 13.2(+/−13.8) |
| Chronic Ligation | 29.3(+/−7.6) | 38.3(+/−19) | 1.9(+/−1.8) | 45.8(+/−19) |

Cavernosometry was performed 6 weeks after castration, 7 days after internal iliac ligation in the acute ligation group, and 30 days after ligation in the chronic ligation group. (* $p \leq 0.05$, for comparison of castration vs. control groups, and castration vs. acute ligation groups)

Experiment 2: Prevention trial: Our second goal was to perform a prevention trial using intracavernosal VEGF either in the form of recombinant protein or virus-directed gene expression vector in an attempt to prevent the development of venogenic erectile ED in castrated animals. As shown in Table 3, flaccid ICP was again in the range of 30 cm $H_2O$ in each of the animal groups. After papavarine administration, however, both control groups (castration only and castration with LacZ injection) exhibited only a weak rise in ICP (5-10 cm $H_2O$), required a significant infusion rate to sustain an erectile ICP of 100 cm $H_2O$, and had a steep pressure drop after the inflow was terminated. In contrast, the 3 treatment groups exhibited nearly normal erectile function with high ICP in response to papavarine, a very low maintenance rate to sustain erectile ICP and minimal pressure drop when the infusion was stopped. Of note, the VEGF gene-treated animals showed marginally less erectile function with a lesser response to papavarine and a higher drop rate than the animals treated with either testosterone replacement or intracavernosal VEGF protein.

TABLE 3

(Experiment 2) Cavernosometric findings in castrated animals after prevention trial of testosterone replacement (C + Testosterone), VEGF protein treatment (C + VEGF), AAV-VEGF gene therapy (C + VEGF gene), or LacZ control (C + LacZ control).

|  | Flaccid ICP (cm $H_2O$) | ICP After Papavarine (cm $H_2O$)* | Maintenance Rate (ml/min)* | Drop Rate in 1 min. (cm $H_2O$)* |
| --- | --- | --- | --- | --- |
| C + salinie | 23.4(+/−5.3) | 29.4(+/−15) | 0.51(+/−0.26) | 56.1(+/−15) |
| C + Testosterone | 28.9(+/−7.5) | 87.7(+/−26) | 0.09(+/−0.1) | 11.7(+/−16) |
| C + VEGF | 27.8(+/−5.2) | 85.0(+/−28) | 0.04(+/−0.09) | 9.0(+/−20) |
| C + VEGF gene | 23.4(+/−7.1) | 61.4(+/−36) | 0.04(+/−0.03) | 27.8(+/−18) |
| C + LacZ | 27.0(+/−6.7) | 36.0(+/−12.8) | 0.25(+/−0.31) | 58.6(+/−8.1) |

Pharmacologic cavernosometry was performed 9 weeks after castration. (*$p \leq 0.05$, comparing castration only to the treatment groups, excluding the LacZ control group.)

Experiment 3: Treatment trial: The third phase was to perform a treatment trial using intracavernosal VEGF in animals with venous leak. The goal was to assess the efficacy of VEGF at reversing established venogenic erectile dysfunction in an animal model. Animals were castrated and then 4-6 weeks later underwent cavernosometry. As shown in Table 4, before VEGF treatment, this animal group displayed a weak response to papavarine with intracorporal pressure reaching 33 cm $H_2O$ compared to normal animals who attain nearly 100 cm $H_2O$ with such treatment (see Table 2). Also, these castrates required a relatively high maintenance rate (0.19 ml/min.) to achieve erectile pressure and a steep drop rate when the infusion was terminated (45.1 cm $H_2O$ in 60 seconds), evidencing venous leak. After these animals received intracorporal VEGF treatment, however, nearly normal erectile function returned with a prompt rise in intracorporal pressure after papavarine (to 84 cm $H_2O$), a low maintenance rate (0.08 ml/min.) to achieve erectile pressure and a minimal drop in intracorporal pressure (17.4 cm $H_2O$ in 60 seconds) after the infusion was terminated.

TABLE 4

(Experiment 3) Cavernosometric findings in VEGF treatment trial.

|  | Flaccid ICP (cm $H_2O$) | ICP After Papavarine (cm $H_2O$)* | Maintenance Rate (ml/min)* | Drop Rate in 1 min. (cm $H_2O$)* |
| --- | --- | --- | --- | --- |
| Before VEGF treatment (6 wks after castration) | 22.4(+/−6.9) | 33.0(+/−12.3) | 0.19(+/−0.18) | 45.1(+/−18) |
| 1 month following VEGF treatment | 25.3(+/−8.5) | 83.9(+/−31) | 0.08(+/−0.15) | 17.4(+/−24) |

Animals were castrated and then shown to have venous leak (after approximately 6 weeks) by pharmacologic cavernosometry. They were then treated with intracavernosal VEGF and one month later underwent repeat cavernosometry. (*$p \leq 0.05$)

Immunohistochemistry: FIGS. 1A-D represent cross-sectional micrographs of the rat penis at the proximal shaft, after immunohistochemistry for alpha actin. Alpha actin, a marker for penile smooth muscle, stains brown and can be seen surrounding the sinusoidal spaces. Qualitatively, we see decreased smooth muscle content in FIG. 1B (6 weeks after castration) compared to FIG. 1A (normal control). In castrates treated with either testosterone replacement (FIG. 1C) or intracavernosal VEGF protein (FIG. 1D) the quantity of smooth muscle returns to normal morphology. Computerized image analysis with Adobe Photoshop was used to quantify the area of immunostaining by counting the number of digitized pixels corresponding to the area of brown staining, thereby providing some numerical comparison of the quantity of smooth muscle in each specimen. This analysis shows the following pixel count: sham (43518), castrated (37214), AAV-VEGF treated (51690), VEGF protein treated (52990).

Transmission Electron Microscopy:

Dorsal nerve: In sham-operated rats (FIG. 2A), the dorsal nerve was filled with both myelinated and non-myelinated nerve bundles. The mean diameter of the individual myelinated axon (excluding myelin sheath) was 2.54±1.04 µm. The mean thickness of the myelin sheath was 0.74±0.21 µm. The mean diameter of the non-myelinated axon was 0.97±0.35 µm. The cytoplasm and nuclei of Schwann cells were seen occasionally near the nerve fibers.

In castrated rats, with or without LacZ injection (FIG. 2B), the diameter of both the myelinated and non-myelinated axons appeared smaller than those of the sham-operated rats. Mean diameters were the following: myelinated axon 1.64±1.0 µm; myelin sheath 0.49±0.13 µm; non-myelinated axon 0.64±0.32 µm. Comparing the castrated rats to the sham-operated rats, the p values were 0.06, 0.004 and 0.001 respectively. Many non-myelinated nerve fibers became indistinct and smaller. There was also an increase in the number of nucleated Schwann cells.

Although many small myelinated nerve fibers were still present in castrated rats treated with VEGF or AAV-VEGF (FIG. 2C), larger fibers with thick myelin sheaths were also noted. The mean diameter of the myelinated nerve and myelin sheath were 2.36±0.92 µm and 0.93±0.44 µm respectively. The non-myelinated nerve fibers were more clearly defined but were not as abundant as the sham group. The mean diameter of non-myelinated axons was 0.96±0.33 µm. Comparing the VEGF-treated group to the castrated+Lac Z group, the p values of myelinated axon, myelin sheath and nonmyelinated axon were 0.113, 0.05 and 0.000 respectively. The nerve fibers and myelin sheath in the testosterone replacement group appeared similar to the sham group.

Intracavernosal Tissues:

Intracavernous smooth muscle cells: In sham-operated rats, the smooth muscle cells (myocytes) were usually arranged in clusters and were separated by fine strands of fibroconnective tissue (FIG. 3A). The cytoplasm of these myocytes contained abundant contractile myofilaments and dense bodies. Occasionally, small aggregates of organelles, including mitochondria, rough endoplasmic reticulum and Golgi apparatus, were found adjacent to the nucleus. The cell membrane (sarcolemma) consisted typically of alternating dense bands and light bands. The light bands contain numerous pinocytotic vesicles (caveolae). The intercellular spaces among myocytes were usually quite narrow with many gap junctions connecting individual cells. Nerve terminal varicosities were frequently seen located near clusters of smooth muscle cells. In low power micrographs (6,500×) of castration with or without LacZ rats, the smooth muscle cells appeared scattered in a field of connective tissues (FIG. 3B). The major differences between the castrated and castrated+ testosterone-treated rats were the increase in cytoplasmic myofilaments and the decrease in intercellular spaces in the latter group of rats. The myocytes in testosterone-treated rats appeared packed in clusters rather than scattered.

Striking differences were noted when comparing the AAV-VEGF and VEGF protein-treated rats to the castrated+Lac Z rats. The smooth muscles were arranged in clusters with minimal intercellular spaces (FIG. 3C). Under high power (9,400×), we noted the following: an increase in myofilaments and dense bodies, a decrease in dense bands, and an increase in the number of caveolae within the light bands of the sarcolemma (FIGS. 3D and E).

Figure 4:
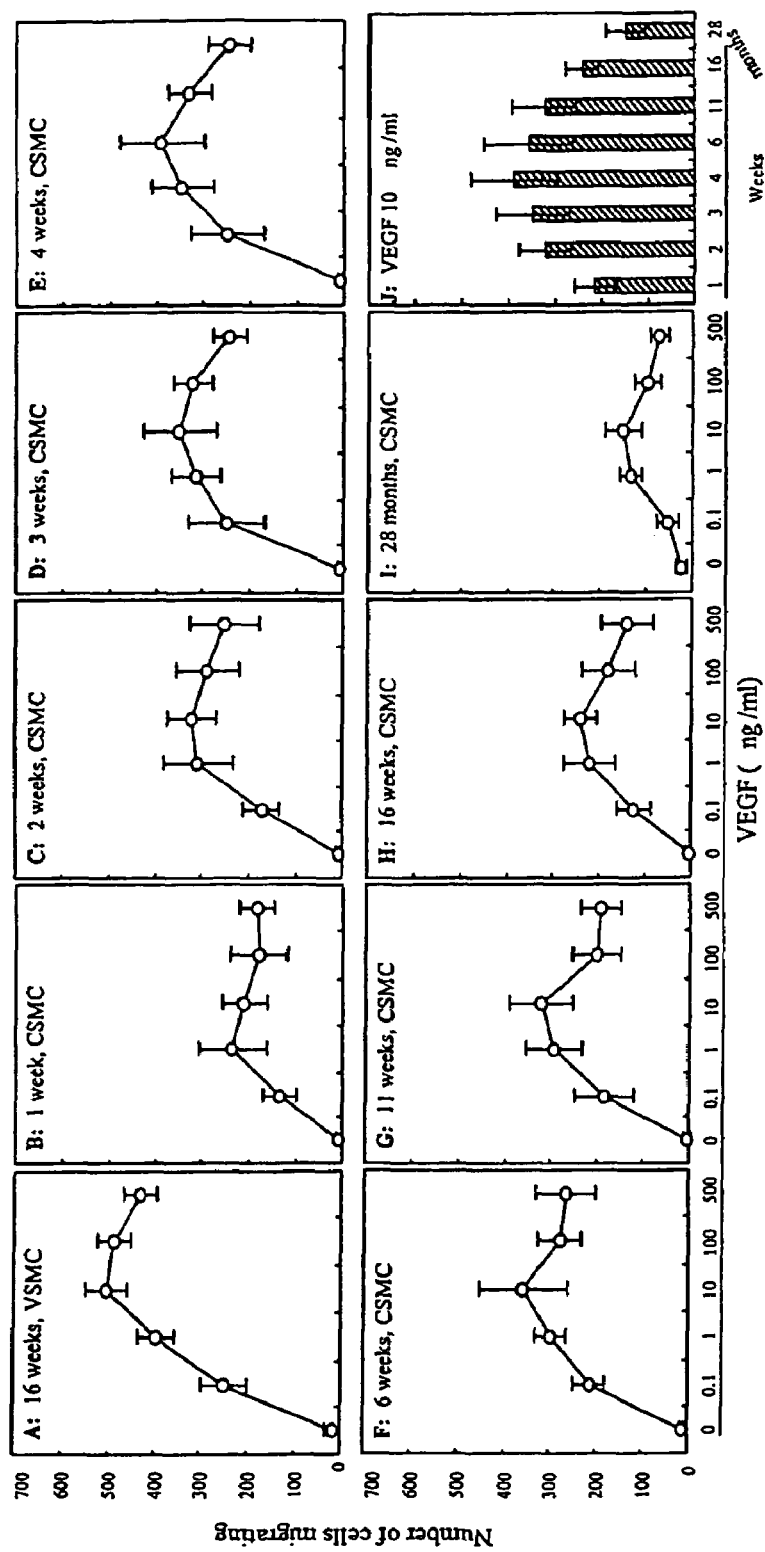
FIG. 4. Effects of VEGF on the mobility of VSMC and CSMC. Equal numbers (8,000) of VSMC (from 16-weeks-old rats, panel A) and CSMC (from rats of indicated ages, panels B to I) were loaded in each well of 24-well Transwell plates and allowed to migrate through a membrane toward a medium containing the indicated concentration of VEGF. Four hours later, the numbers of cells that had migrated through the membrane were counted under a microscope. These numbers are indicated on the left of the panels. Panel J compares the numbers of CSMC (from rats of the indicated ages) that had migrated through the membrane toward media containing the optimal concentration (10 ng/ml) of VEGF.

Endothelial cells: In sham-operated rats (FIG. 4A), the cavernous sinusoids were lined by intact endothelium, the cytoplasm of which contained numerous pinocytotic vesicles (caveolae), mitochondria, rough endoplasmic reticulum, and Golgi apparatus. The nuclei of the endothelial cells were occasionally seen and appeared oval-shaped or elongated. In castration with or without LacZ rats, the appearance of the capillaries and cavernous sinusoidal endothelium was similar to the sham operated group. In AAV-VEGF and VEGF protein-treated rats, the nuclei of the endothelial cells lining most of the capillaries and sinusoids were plump and more numerous, indicative of endothelial hypertrophy and hyperplasia (FIGS. 4B and C).

Enzyme-linked immuno-sorbent assay: The goal of using an adenovirus vector for delivering the VEGF gene is to transfect the penile tissue such that VEGF protein expression may be increase in the penis. To document that the AAV-VEGF treated animals had increased VEGF expression in the penile blood, samples were taken from the penis (penile bleed following glans amputation) and compared with a sample of systemic blood (from the abdominal aorta) for animals groups treated with both AAV-VEGF (n=7) and AAV-LacZ (n=7) (Table 5). While the mean VEGF titer in the systemic serum of animals that did not receive the VEGF gene (AAV-LacZ group) is 9.5±12.6 pg/ml, the AAV-VEGF treated animals demonstrated a marked increase in VEGF titer at 23.3±9.6 pg/ml (p=0.04). Similarly, serum from the penile blood in the AAV-LacZ group had a VEGF titer of 13.6±11.4 pg/ml compared to a mean of 29.7±14.4 pg/ml in the group receiving the intracavernosal VEGF gene (p=0.039). This difference is statistically significant suggesting that increased VEGF expression is occurring in the penile tissue after treatment with AAV-VEGF.

TABLE 5

Results of ELISA for VEGF protein (mean VEGF in pg/ml) in serum samples from animals treated with intracorporal AAV-VEGF (p = 0.03) and AAV-LacZ (p = 0.07)

|  | AAV-VEGF-treated animals | AAV-LacZ-treated animals |
| --- | --- | --- |
| Penile bleed | 29.7 (+/−14.4) | 13.6 (+/−11.4) |
| Systemic blood | 23.3 (+/−9.6) | 9.5 (+/−12.6) |

Discussion

To test our hypothesis, we first developed an animal model of venogenic erectile ED (Experiment 1: Model validation). Mills et al. [10, 11, 26] have previously shown that rats develop venogenic erectile ED within 6-8 days following castration. Animals receiving testosterone repletion maintain an intact veno-occlusive mechanism after castration. These studies were performed using ganglionic electro-stimulation to generate an erection and the penile response gauged with ICP monitoring during either cavernosometry[11] or a penile arterial inflow measurement using a laser Doppler flow[10]. Our goal was to devise a technique for evaluating venous leak in animals similar to the technique used in humans. For this reason, erection was generated using pharmacologic agents (papavarine) instead of ganglionic electro-stimulation. The physiologic parameters (maintenance inflow rate and ICP drop rate) used to diagnose venous leak in humans [27][28] were reproduced in a rat model. Using this technique, pharmaco-cavernsometric findings were determined in normal animals and animals with venogenic and arteriogenic ED. This method was found to be a sensitive and reproducible technique to evaluate penile arterial insufficiency and venous leak in a rat model.

This model was then used to evaluate the efficacy of VEGF, administered intracorporally as recombinant protein or adeno-associated virus gene vector, to prevent the development of venogenic erectile ED (Experiment 2: Prevention trial). It has been previously shown that castration induces an involution of the prostate gland and it's vasculature [13] Furthermore, after testosterone replacement, endothelial cell proliferation is stimulated and both blood flow and vascular volumes are normalized. After castration, prostatic VEGF synthesis is down regulated, as determined by RT-PCR, western blot and immunohistochemical analysis [12]. Also, testosterone induces VEGF synthesis, suggesting that VEGF may be a tissue mediator of androgenic effects on the prostate. The goal of Experiment 2 was to determine if VEGF could prevent the development of venous leak in the rat model. Both testosterone replacement and VEGF treatment maintained erectile function when administered immediately after castration. Animal groups receiving no testosterone replacement or intracorporal AAV-LacZ showed persistent venogenic erectile ED after castration. Histological examination of smooth muscle content and morphology revealed deterioration in both the quality and quantity of penile smooth muscle after castration. Electron microscopic examination also revealed alteration of cell membrane and widening of intercellular spaces. Smooth muscle content as measured by alpha actin staining was normalized in animals receiving either testosterone or VEGF, evidence of preserved smooth muscle integrity with such preventative treatment.

The final phase was a treatment trial (Experiment 3) in which animals were first documented to have venous leak, 6 weeks after castration, and then treated with intracorporal VEGF protein. One month after such treatment, cavernosometry was repeated and restoration of near normal erectile function was found. We believe that this is the first experimental evidence of any medical therapy improving venogenic erectile ED. The exact mechanism by which VEGF improves erectile function is unknown. Nevertheless, we observed clear evidence of restoration of neural and smooth muscle integrity as well as hyperplasia and hypertrophy of endothelial cells after VEGF treatment. Conceivably, increased cavernosal neovascularity may lead to functional or structural changes in the nerve and smooth muscles. Alternatively, the direct effect of VEGF on the nerve and smooth muscle may also play a role since VEGF has been reported to have a direct trophic effect on the penile smooth muscle cells and spinal neurons in culture 14-16.

Nerve function and NOS expression is depressed with androgen ablation, and this may be another target for VEGF action in the penis. Further studies are underway to study the mechanism of VEGF action in the penis.

Conclusion

The technique presented here for pharmacologic cavernosometry is a simple and reproducible method to evaluate vasculogenic ED in a rat model. Normal erectile function and ED due to arterial insufficiency or venous leak may be diagnosed by characteristic cavernosometric findings. Using this technique, the presence of veno-occlusive disease may be diagnosed in animals 6 weeks after either castration or ligation of the internal iliac arteries.

Animals treated with testosterone replacement at the time of castration retain normal erectile function while those without testosterone replacement develop venous leak. If these animals are treated with intracavernosal recombinant VEGF protein or AAV-VEGF at the time of castration, their erectile function is maintained and venous leak is prevented. The mechanism for this is not known at present, but we find a decrease in penile smooth muscle content in the castrated group compared with either the testosterone replacement group or the group receiving intracavernosal VEGF or AAV-VEGF. Penile smooth muscle morphology is uniformly degenerated after castration. Animals treated with the intracorporal AAV-VEGF transfection vector demonstrate significantly more VEGF protein in their penile serum compared to the systemic serum, and markedly more that control animals, indicating an increased expression of penile VEGF in these animals.

When rats with established venogenic ED are treated with one dose of intracavernosal recombinant VEGF protein, their erectile function returns to nearly normal, with reversal of the veno-occlusive defect. Electronmicroscopy revealed endothelial cell hyperplasia and hypertrophy as well as restoration of smooth muscle and neural integrity in the penile tissue after VEGF treatment. Since impairment of erectile nerve, endothelial cell, and the cavernous smooth musculature is the final common pathway of various type of organic ED, VEGF therapy may hold the key to prevention and cure of many forms of ED.

References For Example 2

1 Christ, G. J.: The penis as a vascular organ. The importance of corporal smooth muscle tone in the control of erection. Urol Clin North Am, 22:, 727, 1995.

2. Karadeniz, T., Topsakal, M., Ariman, A. et al.: Judgment of color Doppler ultrasound with respect to cavernous artery occlusion pressure in dynamic infusion cavernosometry when evaluating arteriogenic impotence. Urol Int, 57:, 85, 1996.

3. Nehra, A., Goldstein, I., Pabby, A. et al.: Mechanisms of venous leakage: a prospective clinicopathological correlation of corporeal function and structure. J Urol, 156:, 1320, 1996.

4. Mersdorf, A., Goldsmith, P. C., Diederichs, W. et al.: Ultrastructural changes in impotent penile tissue: a comparison of 65 patients. J Urol, 145:, 749, 1991.

5. Garban, H., Marquez, D., Cai, L. et al.: Restoration of normal adult penile erectile response in aged rats by long-term treatment with androgens. Biol Reprod, 53:, 1365, 1995.

6. Meisel, R. L., O'Hanlon, J. K. & Sachs, B. D.: Differential maintenance of penile responses and copulatory behavior by gonadal hormones in castrated male rats. Horm Behav, 18:, 56, 1984.

7. Zvara, P., Sioufi, R., Schipper, H. M. et al.: Nitric oxide mediated erectile activity is a testosterone dependent event: a rat erection model. Int J Impot Res, 7:, 209, 1995.

8. Lekas, E., Johansson, M., Widmark, A. et al.: Decrement of blood flow precedes the involution of the ventral prostate in the rat after castration. Urol Res, 25:, 309, 1997.

9. Haggstrom, S., Wikstrom, P., Bergh, A. et al.: Expression of vascular endothelial growth factor and its receptors in the rat ventral prostate and Dunning R3327 PAP adenocarcinoma before and after castration. Prostate, 36:, 71, 1998.

10. Mills, T. M., Lewis, R. W. & Stopper, V. S.: Androgenic maintenance of inflow and veno-occlusion during erection in the rat. Biol Reprod, 59:, 1413, 1998.
11. Mills, T. M., Stopper, V. S. & Wiedmeier, V. T.: Effects of castration and androgen replacement on the hemodynamics of penile erection in the rat. Biol Reprod, 51:, 234, 1994.
12. Haggstrom, S., Lissbrant, I. F., Bergh, A. et al.: Testosterone induces vascular endothelial growth factor synthesis in the ventral prostate in castrated rats. J Urol, 161:, 1620, 1999.
13. Franck-Lissbrant, I., Haggstrom, S., Damber, J. E. et al.: Testosterone stimulates angiogenesis and vascular regrowth in the ventral prostate in castrated adult rats [see comments]. Endocrinology, 139:, 451, 1998.
14. Liu X, Lin C-S, Graziottin T, Resplande J and Lue T F: Vascular endothelial growth factor promotes proliferation and migration of cavernous smooth muscle cells. J Urol; 166: 354-360, 2001.
15. Jin K L, Mao X O, Greenberg D A.: Vascular endothelial growth factor: direct neuroprotective effect in vitro ischemia. Proc Natl Acad Sci USA. 97:10242-7, 2000.
16. Sandal M, Sunder F, Kanji M. Vascular endothelial growth factor is a neurotrophic factor which stimulates axonal outgrowth through the flk-1 receptor. Eur J Neurosci: 2000 12:4243-54, 2000.
17. Verdonck, A., De Ridder, L., Kuhn, R. et al.: Effect of testosterone replacement after neonatal castration on craniofacial growth in rats. Arch Oral Biol, 43:, 551, 1998.
18. Parker, C. R., Jr., Ellegood, J. O. & Mahesh, V. B.: Methods for multiple steroid radioimmunoassay. J Steroid Biochem, 6:, 1, 1975.
19. Maeda, Y., Ikeda, U., Ogasawara, Y. et al.: Gene transfer into vascular cells using adeno-associated virus (AAV) vectors. Cardiovasc Res, 35:, 514, 1997.
20. Dong, J. Y., Fan, P. D. & Frizzell, R. A.: Quantitative analysis of the packaging capacity of recombinant adeno-associated virus. Hum Gene Ther, 7:, 2101, 1996.
21. Ferrara, N., Houck, K., Jakeman, L. et al.: Molecular and biological properties of the vascular endothelial growth factor family of proteins. Endocr Rev, 13:, 18, 1992.
22. Stenberg, P. E., Shuman, M. A., Levine, S. P. et al.: Redistribution of alpha-granules and their contents in thrombin-stimulated platelets. J Cell Biol, 98:, 748, 1984.
23. Karadeniz, T., Topsakal, M., Aydogmus, A. et al.: Correlation of ultrastructural alterations in cavernous tissue with the clinical diagnosis vasculogenic impotence. Urol Int, 57:, 58, 1996.
24. Baumgartner, I., Pieczek, A., Manor, O. et al.: Constitutive expression of phVEGF165 after intramuscular gene transfer promotes collateral vessel development in patients with critical limb ischemia [see comments]. Circulation, 97:, 1114, 1998.
25. Symes, J. F., Losordo, D. W., Vale, P. R. et al.: Gene therapy with vascular endothelial growth factor for inoperable coronary artery disease. Ann Thorac Surg, 68:, 830, 1999.
26. Mills, T. M., Dai, Y., Stopper, V. S. et al.: Androgenic maintenance of the erectile response in the rat. Steroids, 64:, 605, 1999.
27. Hatzichristou, D. G., Saenz de Tejada, I., Kupferman, S. et al.: In vivo assessment of trabecular smooth muscle tone, its application in pharmaco-cavernosometry and analysis of intracavernous pressure determinants [see comments]. J Urol, 153:, 1126, 1995.
28. Karadeniz, T., Ariman, A., Topsakal, M. et al.: Value of color Doppler sonography in the diagnosis of venous impotence. Urol Int, 55:, 143, 1995.

Example 3

The Effect of Adeno-Associated Virus-Mediated Brain-Derived Neurotrophic Factor (BDNF) in an Animal Model for Neurogenic Impotence Animals: Male Sprague-Dawley rats (N=34; age, 3 months; weight, 350 to 400 gm.) were divided into two groups: sham (N=10) and experimental (N=24). The rats in the sham group underwent periprostatic dissection and identification of bilateral cavernous nerves without other manipulation; those in the experimental groups underwent bilateral cavernous nerve freezing. Several minutes after surgery, half of the experimental animals (LacZ group, N=12) received intracavernous AAV-LacZ injection, and the remainder (BDNF group, N=12) received AAV-BDNF. Half of the rats in each group were sacrificed at week 4 and the rest at week 8 for collection of penile tissue. In all animals, erectile function was assessed by electrostimulation of the cavernous nerves before sacrifice.

Surgical Procedure and Transfection Technique:

Under intraperitoneal pentobarbital sodium anesthesia (50 mg./kg.), each animal was placed on a heating pad to maintain its body temperature at 37° C. Through a lower abdominal midline incision, the area posterolateral to the prostate was explored. The major pelvic ganglia and the cavernous nerve were identified with an operating microscope (Olympus, 10-40×). In the experimental group, the cavernous nerve was frozen bilaterally for 1 min. with a thermocouple used to control the temperature (5 mm. diameter, Omega HH21 hand-held microprocessor digital thermometer). (Before surgery, the thermocouple had been placed in a 15-ml. disposable centrifuge tube filled with ground dry ice and kept in a thermo-flask [Lab-Line Instruments Inc.] filled with dry ice.) The temperature of the probe at the beginning of the procedure was −80° C., increasing to −50° C. at 1 min. To prevent disruption of the nerve, 0.2 ml. saline was used to disengage the tip of the probe from the nerve before removal.

After the freezing procedure, the right side of the proximal crus was exposed, and 0.05 ml. of either $10^{10}$ AAV-LacZ or $10^{10}$ AAV-BDNF was injected into 12 rats each through a tuberculin syringe with a 30G needle.

Preparation of AAV-BDNF

Cloning of BDNF cDNA. We used RT-PCR to identify BDNF expression in a human neuroblastoma cell line, SK-N-BE(2). We then used a primer pair, 5'-CCCTACAGGTC-GACCAGGTGA-3' (SEQ ID NO:1) and 5'-CTATACAA-CATGGATCCACTA-3' (SEQ ID NO:2), to amplify the coding sequence of BDNF from SK-N-BE(2) cDNA (underlined sequences are designed XhoI and BamHI restriction sites, respectively). After digestion with XhoI and BamHI, the amplified product was cloned into pBluescript (Stratagene Inc., La Jolla, Calif.) and fully sequenced. The BDNF cDNA was then re-cloned into pcDNA4, a modified version of pcDNA3 plasmid (Invitrogen, Inc., Carlsbad, Calif.) that contains the cytomegalovirus (CMV) promoter for driving the expression of BDNF in mammalian cells.

Construction of rAAV-BDNF. The above pcDNA4BDNF was digested with Sal1 to release the expression cassette containing cytomegalovirus immediate-early (CMVie) promoter, BDNF gene and bovine growth hormone (BGH)

poly-A signal. This expression cassette was inserted into an AAV vector, pAV53, resulting in the construction of rAAV-BDNF.

Virus production and titration. rAAV-BDNF was produced by a three-plasmid co-transfection method. Twenty 15-cm plates of 293 cells (50 to 60% confluent) were maintained in Dulbecco modified Eagle medium (DMEM, Gibco) supplemented with 10% fetal bovine serum (Hyclone) and 25 mM. HEPES and co-transfected by the calcium phosphate method with a total of 45 µg. DNA, 15 µg. of AAV-BDNF vector, and 15 µg. each of pLHP 19 (AAV helper plasmid) and pLadeno5 (adenovirus helper plasmid), kindly provided by AVIGEN. Six hours after transfection, the medium was replaced with fresh DMEM containing 1% fetal bovine serum. The cells were harvested at 48 h posttransfection by centrifugation (1000 g for 10 min.), and the cell pellets were re-suspended in 0.1 M. Tris-HCL, 0.15 M. NaCl solution (PH 8.0) and subjected to four cycles of freeze-thaw and removal of cell debris. Large-scale rAAV CsCl purification was carried out as described previously.[12] AAV-BDNF vector titer was determined by quantitative dot blot hybridization of DNase-treated stocks. The AAV vector titer used in the experiment refers to the particle number of AAV vector genomes in the sample as determined by the quantitative dot blot assay.

Functional Evaluation and Tissue Procurement

At weeks 4 and 8 postoperatively, rats in each group were re-explored for direct electrostimulation of the cavernous nerves before tissue collection. The skin overlying the penis was incised and the ischiocavernous muscle was partly removed to expose both penile crura. A 23G butterfly needle connected to PE-50 tubing was inserted in the right crus for pressure measurement. Electrostimulation was performed with a delicate stainless-steel bipolar hook electrode attached to a multi-jointed clamp. (Each pole was 0.2 mm. in diameter; the two poles were separated by 1 mm.) Short wave pulses were generated by a Macintosh computer with a custom-built constant current amplifier. Stimulus parameters were 1.5 mA., frequency 20 Hz., pulse width 0.2 m sec., duration 50 sec. Each cavernous nerve was stimulated and intracavernous pressures were measured and recorded with a Macintosh computer programmed with LabVIEW 4.0 software (National Instruments, Austin, Tex.). The pressure for each animal was determined by the mean of both sides.

NADPH Diaphorase Staining

After sacrifice, samples of major pelvic ganglia and penile tissue were fixed for 3 hours in a cold, freshly prepared, solution of 2% formaldehyde, 0.002% picric acid in 0.1 M. phosphate buffer, pH 8.0. Tissues were cryoprotected for 24 hours in cold 30% sucrose in 0.1 M. phosphate buffer, pH 8.0. They were then embedded in O.C.T. compound (Tissue-Tek, Miles Laboratory), frozen in liquid nitrogen, and stored at −70° C. Cryostat tissue sections were cut at 10 µm., adhered to charged slides, air-dried for 5 min., and hydrated for 5 min. with 0.1 M. $PO_4$, pH 8.0. Sections were incubated with 0.1 mM. NADPH, 0.2 mM. nitroblue tetrazolium, 0.2% Triton X-100 in 0.1 M. $PO_4$, pH 8.0, for 60 min. at room temperature. The reaction was terminated by washing in buffer. Slides were then coverslipped with buffered glycerin as the mounting medium.[13]

The presence of NADPH diaphorase-positive nerves was evidenced as a blue stain in the major pelvic ganglia, dorsal nerves and cavernous tissue, and the staining pattern was assessed by counting the number of positive neurons in 4 random fields (magnification 400×). The percentage of darkly and lightly stained cells in the major pelvic ganglia was calculated by dividing the number of these cells by the total number of positive cells.

Nitric Oxide Synthase Antibody Staining

Tissue fixation was the same as with NADPH-diaphorase specimens. After freezing, 10-µm. cryostat tissue sections were adhered to charged slides, air-dried, and hydrated for 5 minutes. with 0.05M. sodium phosphate buffer (PBS, pH 7.4). Sections were treated with hydrogen peroxide/methanol to quench endogenous peroxidase activity. After rinsing with water, sections were washed twice in PBS for 5 min. followed by 30 min. of room-temperature incubation with 3% horse serum/PBS/0.3% triton X-100. After draining solution from sections, tissues were incubated for 60 min. at room temperature with mouse monoclonal anti-nNOS (Transduction Laboratories, Lexington, Ky.) at a 1:500 dilution. After washing for 5 min. with PBS/TX and then for 5 min. twice with PBS alone, sections were immunostained with the avidin-biotin-peroxidase method (Elite ABC, Vector Labs, Burlingame Calif.), with diaminobenzidine as the chromagen, followed by counterstaining with hematoxylin.

Statistical Analysis

The nonparametric Mann-Whitney U and ANOVA tests with Statview 4.02 software were used to compare results. Values were considered significant at $p<0.05$.

Results

Functional Studies

In both the LacZ and BDNF groups, maximal intracavernous pressure in response to bilateral cavernous nerve electrostimulation was less than in the sham group. However, the pressure in the BDNF group was significantly higher than in the LacZ group at both 4 and 8 weeks (FIG. 1 and Table 6).

TABLE 6

Maximal intracavernous Pressure In Response to Electrostimulation 4 and 8 Weeks After Bilateral Cavernous Nerve Freezing

| Time (Weeks) | Sham Operation (n = 10) | LacZ (n = 12) | BDNF (n = 12) |
|---|---|---|---|
| 4 | 105 ± 10.5* | 28.4 ± 5.5 | 585. ± 11.7† |
| 8 | 115.5 ± 7.7 | 37.7 ± 7.9 | 61.3 ± 12.5† |

*All values are expressed as cm H2O; mean ± SD
†p < 0.05 v. LacZ.

NADPH Diaphorase Staining

Dorsal nerve. At week 4, the LacZ group showed significantly fewer NADPH diaphorase-positive nerve fibers than did the BDNF group. At week 8, the number had increased in both groups, but there were still significantly fewer in the LacZ group When compared with the sham group, both experimental groups showed fewer positive nerve fibers (Table 7).

TABLE 7

NADPH Diaphorase-positive Nerve Fibers In the Dorsal Nerve and Cavernous Tissue

| Time (Weeks) | Sham Operation (N = 10) | LacZ (N = 12) | BDNF (N = 12) |
|---|---|---|---|
| | Dorsal Nerve | | |
| 4 Weeks | 138.5 ± 10.5* | 45.7 ± 5.8 | 65.5 ± 15.5† |
| 8 Weeks | 140.2 ± 9.8 | 55.6 ± 8.4 | 86.4 ± 12.2† |

TABLE 7-continued

NADPH Diaphorase-positive Nerve Fibers In the
Dorsal Nerve and Cavernous Tissue

| Time (Weeks) | Sham Operation (N = 10) | LacZ (N = 12) | BDNF (N = 12) |
|---|---|---|---|
| Cavernous Tissue | | | |
| 4 Weeks | 103 ± 9.8 | 25.5 ± 3.6 | 45.5 ± 10.5† |
| 8 Weeks | 110.2 ± 10.5 | 35.6 ± 10.4 | 66.1 ± 15.2† |

*All values expressed as Mean ± S.D.
†$p < 0.05$ vs. LacZ

Intracavernous nerves. Histologic evaluation showed significantly fewer NADPH diaphorase-positive nerve fibers in the trabecular smooth muscle of the LacZ group than in the BDNF group at both 4 and 8 weeks. When compared with the sham group, both experimental groups had significantly fewer (Table 7).

Major pelvic ganglia. At week 4, most of the neurons in the major pelvic ganglia in the LacZ group exhibited a lighter staining pattern than that seen in the BDNF group. In addition, at 8 weeks most of these LacZ neurons had irregular cell contour and multiple vacuoles in the cytoplasm. The percentage of darkly stained cells in the BDNF group at both time points was significantly higher than in the LacZ group, and their appearance (i.e. smooth contour and very few vacuoles in the cytoplasm) was similar to that in the sham group. In both experimental groups, the percentage of darkly stained cells was significantly less than in the sham group (Table 8).

TABLE 8

NADPH Diaphorase-positive Neurons in the Major Pelvic Ganglion

| Time | Group | Dark Stain | Light Stain | Total | % Dark Stain | % Light Stain |
|---|---|---|---|---|---|---|
| 4 Weeks | Sham | 102 ± 0.5* | 21.7 ± 3.5 | 123.5 ± 4.5† | 82.2 ± 5.3 | 17.3 ± 6.8 |
| | LacZ | 32.4 ± 15.2 | 52.5 ± 20.4 | 85 ± 20.1 | 38.5 ± 17.2 | 60.7 ± 17.2 |
| | BDNF | 61.8 ± 23.7 | 33.8 ± 9 | 95.7 ± 22.4 | 62.1 ± 13.1‡ | 38.6 ± 11.8 |
| 8 Weeks | Sham | 101 ± 12.3 | 25.5 ± 5.5 | 136.7 ± 11.3† | 80.7 ± 9.8 | 19.2 ± 4.5 |
| | LacZ | 45 ± 12.7 | 53.3 ± 9.5 | 98.5 ± 14.3 | 45.8 ± 0.8 | 54.1 ± 0.8 |
| | BDNF | 69.4 ± 21.1 | 38.4 ± 14 | 107.8 ± 23.58 | 64.3 ± 10.7‡ | 35.6 ± 10.7 |

*All values expressed as Mean ± S.D.
†$p < 0.05$ vs. either experimental group
‡$p < 0.05$ vs. LacZ group nNOS Immunostaining Immunostaining of penile tissue and the major pelvic ganglia for nNOS revealed positive staining in the same nerve fibers and neurons as with NADPH diaphorase. The neurons of the major pelvic ganglia of the LacZ group showed lighter staining patterns and many more vacuoles in the cytoplasm than did the neurons in the BDNF and sham groups.

Discussion

The aim of the present study was to investigate the feasibility of using AAV-BDNF gene transfer to facilitate recovery of potency after bilateral cavernous nerve injury. Our past studies have led us to believe that bilateral cavernous nerve freezing in the rat is a suitable model for such injury because the neural sheath is preserved, as it is in patients undergoing nerve-sparing prostatectomy or cryoablation. In addition, the course and extent of functional recovery have been well documented in this model.[14] We used maximal intracavernous pressure in response to cavernous nerve electrostimulation to assess recovery of erectile function. Although apomorphine-induced erection may be more physiologic, we do not believe it can reliably differentiate partial from full erection in rats with cavernous nerve injury.

In this study, the number of nNOS-containing neurons in the major pelvic ganglia of both experimental groups was less than in the sham group. However, the percentage of darkly stained neurons was significantly greater in the BDNF group than in the LacZ group at both 4 and 8 weeks. Moreover, most neurons of the BDNF and sham groups did not show the cytoplasmic vacuoles and irregular cell contour seen in the LacZ group. These findings suggest that the production of BDNF protein in penile tissue can be retrogradely transported to the major pelvic ganglia to prevent neuronal damage and preserve nNOS enzymes in the neurons. This in turn facilitates the recovery of erectile function, as evidenced by the more numerous nNOS-positive nerve fibers in the erectile tissue and higher intracavernous pressure in the BDNF group.

A previous study has shown a significantly increased survival of motoneurons 1 week after axotomy in animals pre-treated with adenovirus-encoding BDNF or glial cell line-derived neurothrophic factor (GDNF).[17] However, because of the disadvantages of the adenovirus, we used adeno-associated virus (AAV), a unique member of the non-enveloped, single-stranded-DNA Parvovirus that possesses several properties that distinguish it from other gene-transfer vectors. Its advantages include stable and efficient integration of viral DNA into the host genome,[18] lack of associated human disease,[19] broad host range, ability to infect growth-arrested cells,[20] and ability to carry non-viral regulatory sequences without interference from the viral genome.[21] In addition, no superinfection inhibition is associated with AAV vectors.[18] The infected cells are spread several millimeters around the needle tract. AAV is able to infect axon terminals and is retrogradely transported. Injection of AAV vector expressing LacZ into several brain regions has shown the presence of transgene expression as early as 24 hours,[22] lasting (at significantly decreased levels) as long as 6 months.

The penis is a convenient organ for gene therapy because of its external location and slow circulation in the flaccid state. In addition, its sinusoidal structure and the gap junctions between smooth muscles ensure wide distribution of injected vectors. To our knowledge, this is the first demonstration of gene therapy with AAV-BDNF used to facilitate the recovery of nNOS-containing nerves and neurons and consequent erectile function. Because our previous studies have shown that 3 to 6 months may be required for more complete regeneration of cavernous nerves and erectile function in both unilateral resection and unilateral freezing models,[3,16] we are presently conducting a further study to examine the effects of higher AAV-BDNF titer and longer follow-up in this model.

Conclusion

Our results showed that intracavernous injection of AAV-BDNF after freezing of bilateral cavernous nerves had the following effects: 1) facilitated the recovery of erectile function, 2) enhanced the regeneration of the intracavernous and dorsal nerves, and 3) prevented neuronal degeneration in the major pelvic ganglia. If further studies confirm its effectiveness and safety, intracavernous injection of neurotrophins or other growth factors has the potential to be a curative therapy for neurogenic erectile dysfunction after cryoablation or radical pelvic surgery.

References For Example 3

1. Walsh, P. C., and Mostwin, J. L.: Radical prostatectomy and cystoprostatectomy with preservation of potency. Results using a new nerve-sparing technique. Br. J. Urol., 56: 694, 1984.
2. Paick, J. S., Donatucci, C. F., and Lue, T. F.: Anatomy of cavernous nerves distal to prostate: microdissection study in adult male cadavers. Urology, 42: 145, 1993.
3. Carrier, S., Zvara, P., Nunes, L., Kour, N. W., Rehman, J., and Lue, T. F.: Regeneration of nitric oxide synthase-containing nerves after cavernous nerve neurotomy in the rat. J. Urol. 153: 1722, 1995.
4. Jung, G. W., Spencer, E. M., and Lue, T. F.: Growth hormone enhances regeneration of nitric oxide synthase-containing penile nerves after cavernous nerve neurotomy in rats. J. Urol. 160: 1899, 1998.
5. Leibrock, J., Lottspeich, F., Hohn, A., Hofer, M., Hengerer, B., Masiakowski, P., Thoenen, H., and Barde, Y. A.: Molecular cloning and expression of brain-derived neurotrophic factor. Nature. 341: 149, 1989.
6. Ide, C.: Peripheral nerve regeneration. Neurosci. Res. 25: 101, 1996.
7. DiStefano, P. S., Friedman, B., Radziejewski, C., Alexander, C., Boland, P., Schick, C. M., Lindsay, R. M., and Wiegand, S. J.: The neurotrophins BDNF, NT-3, and NGF display distinct patterns of retrograde axonal transport in peripheral and central neurons. Neuron. 8: 983, 1992.
8. Oppenheim, R. W., Yin, Q. W., Prevette, D., and Yan, Q.: Brain-derived neurotrophic factor rescues developing avian motoneurons from cell death. Nature. 360: 755, 1992.
9. Yan, Q., Elliott, J., and Snider, W. D.: Brain-derived neurotrophic factor rescues spinal motor neurons from axotomy-induced cell death. Nature. 360: 753, 1992.
10. Meyer, M., Matsuoka, I., Wetmore, C., Olson, L., and Thoenen, H.: Enhanced synthesis of brain-derived neurotrophic factor in the lesioned peripheral nerve: different mechanisms are responsible for the regulation of BDNF and NGF mRNA. J. Cell Biol. 119: 45, 1992.
11. Nonomura, T., Nishio, C., Lindsay, R. M., and Hatanaka, H.: Cultured basal forebrain cholinergic neurons from postnatal rats show both overlapping and non-overlapping responses to the neurotrophins. Brain Res. 683: 129, 1995.
12. Matsushita, T., Elliger, S., Elliger, C., Podsakoff, G., Villarreal, L., Kurtzman, G. J., Iwaki, Y., and Colosi, P.: Adeno-associated virus vectors can be efficiently produced without helper virus. Gene Ther. 5: 938, 1998.
13. Alm, P., Larsson, B., Ekblad, E., Sundler, F., and Andersson, K. E.: Immunohistochemical localization of peripheral nitric oxide synthase-containing nerves using antibodies raised against synthesized C- and N-terminal fragments of a cloned enzyme from rat brain. Acta Physiol. Scand. 148: 421, 1993.
14. Korsching, S.: The neurotrophic factor concept: a reexamination. J. Neurosci. 13: 2739, 1993.
15. Lewin, G. R. and Barde, Y. A.: Physiology of the neurotrophins. Annu. Rev. Neurosci. 19: 289, 1996.
16. El-Sakka, A. I., Hassan, M. U., Selph, C., Perinchery, G., Dahiya, R., and Lue, T. F.: Effect of cavernous nerve freezing on protein and gene expression of nitric oxide synthase in the rat penis and pelvic ganglia. J. Urol. 160: 2245, 1998.
17. Gimenez y Ribotta, M., Revah, F., Pradier, L., Loquet, I., Mallet, J., and Privat, A.: Prevention of motoneuron death by adenovirus-mediated neurotrophic factors. J. Neurosci. Res. 48: 281, 1997.
18. McLaughlin, S. K., Collis, P., Hermonat, P. L., and Muzyczka, N.: Adeno-associated virus general transduction vectors: analysis of proviral structures. J. Virol. 62: 1963, 1988.
19. Berns, K. I., Cheung, A., Ostrove, J., and Lewis, M.: Adeno-associated virus latent infection. In: B. W. J. Mahy, A. C. Minson, and G. K. Darby (eds.), Virus Persistence. Cambridge, UK: Cambridge University Press, 1982.
20. Podsakoff, G., Wong, K. K., Jr., and Chatterjee, S.: Efficient gene transfer into nondividing cells by adeno-associated virus-based vectors. J. Virol. 68: 5656, 1994.
21. Miller, J. L., Walsh, C. E., Ney, P. A., Samulski, R. J., and Nienhuis, A. W.: Single-copy transduction and expression of human gamma-globin in K562 erythroleukemia cells using recombinant adeno-associated virus vectors: the effect of mutations in NF-E2 and GATA-1 binding motifs within the hypersensitivity site 2 enhancer [published erratum appears in Blood 1995 Feb. 1;85(3):862]. Blood. 82: 1900, 1993.
22. During, M. J. and Leone, P.: Adeno-associated virus vectors for gene therapy of neurodegenerative disorders. Clin. Neurosci. 3: 292, 1995.

Example 4

Vascular Endothelial Growth Factor Promotes Proliferation and Migration of Cavernous Smooth Muscle Cells Animals. Male Wistar rats were obtained from Charles River Laboratories (Wilmington, Mass.). Young rats were 1, 2, 3, 4, 6, 11, and 16 weeks of age. Old rats were 28 months of age.

Regents. All chemicals were from Sigma-Aldrich Co. (St. Louis, Mo.) unless noted otherwise. Recombinant human $VEGF_{165}$ was from Calbiochem Biosciences Inc. (La Jolla, Calif.). Fetal bovine serum (FBS) and Trypsin-EDTA were from Life Technologies, Inc. (Grand Island, N.Y.). All other cell culture regents were obtained from Cell Culture Facility, University of California, San Francisco.

Cell culture. Each primary culture of CSMC was prepared from the corpora cavernosa of 2-3 rats by the following procedure. The penis was cleared of the urethra, blood vessels, fat and connective tissue. The remaining smooth muscle tissue was washed 3 times in sterile PBS (phosphate-buffered saline) and cut into 2-3 $mm^3$ segments. The segments were placed evenly onto a 100-mm cell culture dish (Falcon-Becton Dickinson Labware, Franklin Lakes, N.J.) inside a cell culture hood. Approximately 10 min later, 10 ml of Dulbecco's Modified Eagle Medium (DMEM) containing penicillin (100 units/ml), streptomycin (100 µg/ml), and 10% FBS was carefully pipetted into the dish. The dish was then kept undisturbed in a humidified 37° C. incubator with 5% $CO_2$. Five days later, tissue segments that have detached from the dish were removed, and the medium was replaced with fresh medium. Another 5 days later, all tissue segments were removed and the medium was again replaced with fresh medium. When small islands of cells were noticeable, they were trypsinized and transferred to a fresh culture dish. Expansion of each cell strain was continued with change of medium every 3 days and passages (trypsinization and seeding) approximately every 10 days. All cells used in the following experiments were from passages 4 through 10. Primary aorta SMC cultures were prepared similarly with aortas isolated from 16-week-old male rats. All cell cultures were confirmed for their smooth muscle identity by an indirect immunofluoresence staining with an anti-smooth muscle myosin heavy chain antibody (Sigma-Aldrich Co. St. Louis, Mo.).

Quantification of VEGF. Each CSMC from rats of different ages was seeded at $4 \times 10^5$ cells per well in 3 ml of DMEM with 10% FBS in 6-well culture plates. Seventy-two hr later, the medium was removed for quantification of VEGF and the cells were trypsinized for the determination of cell number. For quantifying VEGF in the medium, the Mouse VEGF Imununoassay Kit (R&D Systems, Minneapolis, Minn.), which reacts with rat VEGF but not with bovine VEGF, was used. All assays were performed in duplicate in each experiment and all data presented in the Results section are the average of three independent experiments.

Proliferation assay. Cell proliferation assays were performed with the CellTiter-96 kit from Promega Inc. (Madison, Wis.). Each SMC strain from different-aged rats was assayed in one flat-bottom 96-well cell culture plate. The plate was divided into 12 rows that contained VEGF at concentrations from 0 to 100 ng per ml of serum-free DMEM (supplemented with 0.1% BSA). Each well in the same row received 50 µl of the medium containing the same concentration of VEGF. Thereafter, SMC that were grown to 70% confluence were rinsed twice with PBS, trypsinized, and resuspended in serum-free DMEM (supplemented with 0.1% BSA) at 100,000 cell per ml. Aliquots of 50 µl of the cell suspension were then transferred to the 96-well plate so that each well contained 5,000 cells in a final volume of 100 µl. The plate was incubated in a 37° C., humidified incubator with 5% $CO_2$. Three days later, 20 µl of CellTiter 96® AQueous One Solution Reagent was added to each well. After 4 hr of further incubation at 37° C. in the humidified, 5% $CO_2$ incubator, color development, which reflects cell numbers, was recorded with a plate reader (Molecular Devices Corp., Sunnyvale, Calif.) at 490-nm absorbance. For proliferation assays concerning concentrations of FBS in the growth medium, the assay procedure was the same except that different amounts of FBS, instead of VEGF, were added to the medium. All assays were performed in duplicate in each experiment and all data presented in the Results section are the average of three independent experiments.

Migration assay. Cell migration assays were performed in 6.5-mm Transwell chambers of Corning Costar Corporation (Cambridge, Mass.). The Transwell inserts (upper chambers) were bathed in a solution containing 13.4 µg/ml fibronectin in PBS at 37° C. for 1 hr and allowed to air-dry. The dried upper chambers were then placed in the lower chambers, each of which contained 700 µl of serum-free DMEM supplemented with 0.1% BSA and 0 to 500 ng/ml of VEGF. SMC that had been grown to 70% confluence were further conditioned in serum-free DMEM (containing 0.1% BSA) for 2 hr and then trypsinized. The trypsinized cells were washed in PBS and resuspended at a concentration of 80,000 cells per ml in serum-free DMEM (containing 0.1% BSA). One hundred µl of the cell suspension was then added to each upper chamber. After 4 hr of incubation at 37° C., all liquid in the upper and lower chambers was removed by aspiration. The membranes in the upper chambers were subsequently fixed in 1% buffered formalin for 5 min and stained with 2% crystal violet. Non-migratory cells on the upper side of the membranes were scraped off with cotton swabs. Well locations were marked on the membranes and total cells per well were counted visually in a masked fashion. Well locations were then correlated with the concentrations of VEGF in the wells. All assays were performed in duplicate in each experiment and all data presented in the Results section are the average of three independent experiments.

RNA preparation. Cultured cells and rat tissues were homogenized in Tri-Reagent RNA extraction solution (Molecular Research Center, Cincinnati, Ohio). Following the recommended procedure by the supplier, RNAs were further treated with Dnase I to remove traces of contaminating DNA. Quantity and integrity of RNAs were examined by spectrophotometry and agarose gel electrophoresis, respectively. Human heart RNAs were purchased from Clontech Laboratories, Inc. (Palo Alto, Calif.).

RT-PCR analysis. RT-PCR (reverse transcription-polymerase chain reaction) was performed in an RT step and a PCR step. In the RT step, the cellular mRNAs were reverse-transcribed into a "library" of complementary DNAs (cDNAs). This cDNA library was then used for the analysis of various genes in the PCR step. The RT procedure was performed with the SuperScript reverse transcriptase (Life Technologies, Inc., Gaithersburg, Md.) and its accompanying reagents. Briefly, 2.5 µg of each tissue RNA was annealed to 0.4 µg of oligo-dT primer in a 12 µl volume. Four µl of 5× buffer, 2 µl of 0.1 M DTT, 1 µl of 10 mM dNTP, and 1 µl of SuperScript reverse transcriptase were then added to bring the final reaction volume to 20 µl. After one hour of incubation at 42° C., the RT mixture was incubated at 70° C. for 10 min to inactivate the reverse transcriptase. Eighty µl of TE buffer was then added to make a 5× diluted library. A portion of this library was further diluted to various concentrations (up to 100× dilution). One µl of each dilution was then used in a 10 µl PCR to identify the optimal input within the linear amplification range. In addition to the 1 µl diluted library, the PCR mixture consisted of 10 ng of each of a primer pair and reagents supplied with the Taq polymerase (Life Technologies, Inc., Gaithersburg, Md.). PCR was performed in the DNA Engine thermocycler (MJ Research, Inc., Watertown, Mass.) under calculated temperature control. The cycling program was set for 35 cycles of 94° C., 5 sec; 55° C., 5 sec; 72° C., 10 sec, followed by one cycle of 72° C., 5 min. The PCR products were electrophoresed in 1.5% agarose gels in the presence of ethidium bromide, visualized by UV fluorescence, and recorded by a digital camera connected to a computer.

TABLE 9

Oligonucleotide primers

| Gene | Primer name | Sequence | Size of PCR product |
|---|---|---|---|
| β-Actin | Actin-s | 5'-TCTACAATGAGCTGCG TGTG-3' (SEQ ID NO: 3) | 368 bp |
| | Actin-a | 3'-AATGTCACGCACGATT TCCC-5' (SEQ ID NO: 4) | |

TABLE 9-continued

Oligonucleotide primers

| Gene | Primer name | Sequence | Size of PCR product |
|---|---|---|---|
| VEGFR-1 | VEGFR-1s | 5'-ATGCTGGATTGCTGGC ACA-3' (SEQ ID NO: 5) | 323 bp |
|  | VEGFR-1a | 3'-TCAAACATGGAGGTGG CATT-5' (SEQ ID NO: 6) |  |
| VEGFR-2 | VEGFR-2s | 5'-GCCTTTGGCCAAGTGA TTGA-3' (SEQ ID NO: 7) | 479 bp |
|  | VEGFR-2a | 3'-TCCAAGGTCAGGAAGT CCTT-5' (SEQ ID NO: 8) |  |

Oligonucleotide primers. Primer pairs for RT-PCR analysis of VEGFR-1, VEGFR-2 and β-actin genes are listed in Table 9. They were designed to recognize the respective mRNAs in both humans and rats.

Western blot analysis. Cultured cells were lysed in a buffer containing 1% IGEPAL CA-630, 0.5% sodium deoxycholate, 0.1% SDS, 10 µg/ml aprotinin, 10 µg/ml leupeptin, and 1× PBS. Cell lysates containing indicated amounts of protein were electrophoresed in 7.5% SDS-PAGE and then transferred to PVDF membrane. The membrane was stained with Ponceau S to verify the integrity of the transferred proteins and to monitor the unbiased transfer of all protein samples. Detection of VEGFR-1 protein on the membrane was performed with the ECL kit (Amersham Life Sciences Inc., Arlington Heights, Ill.) using an anti-VEGFR-1 rabbit serum from Santa Cruz Biotech, Inc. (Santa Cruz, Calif.).

Results

Growth rates of CSMC from different-aged rats. Like most other cultured cells, our rat CSMC were maintained in a medium supplemented with 10% FBS. However, because certain experiments may require the use of media containing lower concentrations of FBS, we wished to know the differences between different age groups in their growth rates under different concentrations of FBS. All cells, regardless of the ages of rats from which they were derived, grew at increasing rates with increasing FBS concentrations. At lower concentrations of FBS (0 and 2.5%), the growth rates showed little differences between different age groups. However, at higher concentrations of FBS (5 and 10%), differences in growth rates became more pronounced. In particular, cells from 4-week-old rats seemed to respond best to higher concentrations of FBS and cells from 28-month-old rats least well.

Figure 2:
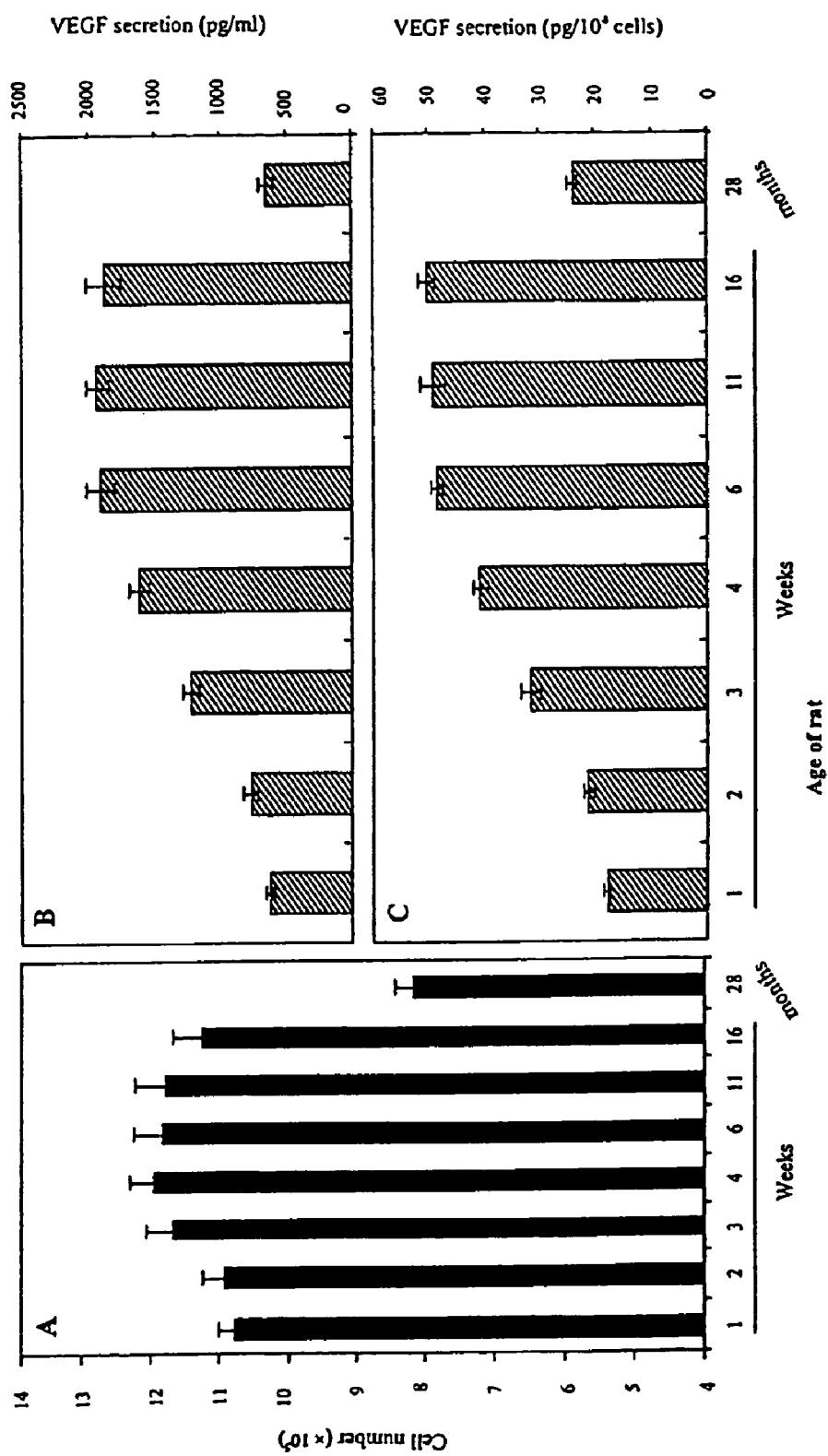
FIG. 2. Quantification of VEGF secreted by CSMC. Equal number ($4 \times 10^5$) of CSMC from different-aged rats were seeded in each well of 6-well plates and allowed to grow for three days in medium containing 10% of FBS. The medium from each well was then assayed for the concentration of rat-specific VEGF (panel B) and the cell number was determined (panel A). The calculated amount of VEGF in each well was then divided by the number of cells in each well to derive the data shown in panel C.

VEGF secretion by CSMC from different-aged rats. VSMC have been shown to be the principal source of secreted VEGF in the vascular (aorta) system. Pueyo, et al., *Exp. Cell Res.*, 238: 354 (1998). We therefore examined our rat CSMC for their ability to produce VEGF. We chose 72 hr after seeding the cells as the point of time to assay for the secreted VEGF. Because CSMC from different age groups grew at different rates, we also determined the cell numbers for each of the tested cells. When the concentrations of the secreted VEGF were adjusted for the numbers of cells at the time of assay (FIG. 2A), it is apparent that, within the young rat groups (ages 1 to 16 weeks), CSMC from more matured rats secreted more VEGF than CSMC from less matured rats (FIG. 2C). However, CSMC from old rats (28 months old) produced similar amounts of VEGF as those from the very young rats (1 and 2 weeks old).

Effects of VEGF on cell growth. It has been reported that VEGF did not stimulate growth of VSMC. Grosskreutz, et al., *Microvasc. Res.*, 58: 128 (1999). This observation was confirmed with VSMC from 16-weeks-old rats (FIG. 3A). However, CSMC from all ages of rats responded to VEGF in the form of cell proliferation. Their growth rates increased with increasing concentrations of VEGF up to 12.5 ng/ml, and after which, the cell growth rate started to decline with increasing concentrations of VEGF (FIG. 3B-I). When compared at the optimal dosage (12.5 ng/ml) of VEGF, all cells from young rats (1 to 16 weeks old) outgrew cells from the old rats (28 months) and the peak growth occurred with cells from 11-weeks-old rats (FIG. 3J).

Effects of VEGF on cell motility. It has been reported that VEGF stimulated migration of VSMC. Grosskreutz, et al., *Microvasc. Res.*, 58: 128 (1999). This observation was confirmed with VSMC from 16-weeks-old rats (FIG. 4A). Similarly, VEGF stimulated migration of CSMC from both young and old rats in a dose-dependent manner up to the 10 ng/ml point (except the 1-week-old, which peaked at 1 ng/ml). At higher concentrations (100 and 500 ng/ml) of VEGF, the mobility of all tested cells started to decline (FIGS. 4B-I). When compared at the optimal dosage (10 ng/ml) of VEGF, all cells from young rats (1 to 16 weeks old) out-migrated cells from the old rats (28 months) and the peak migration rate occurred with cells from 4-weeks-old rats (FIG. 4J).

Figure 3:
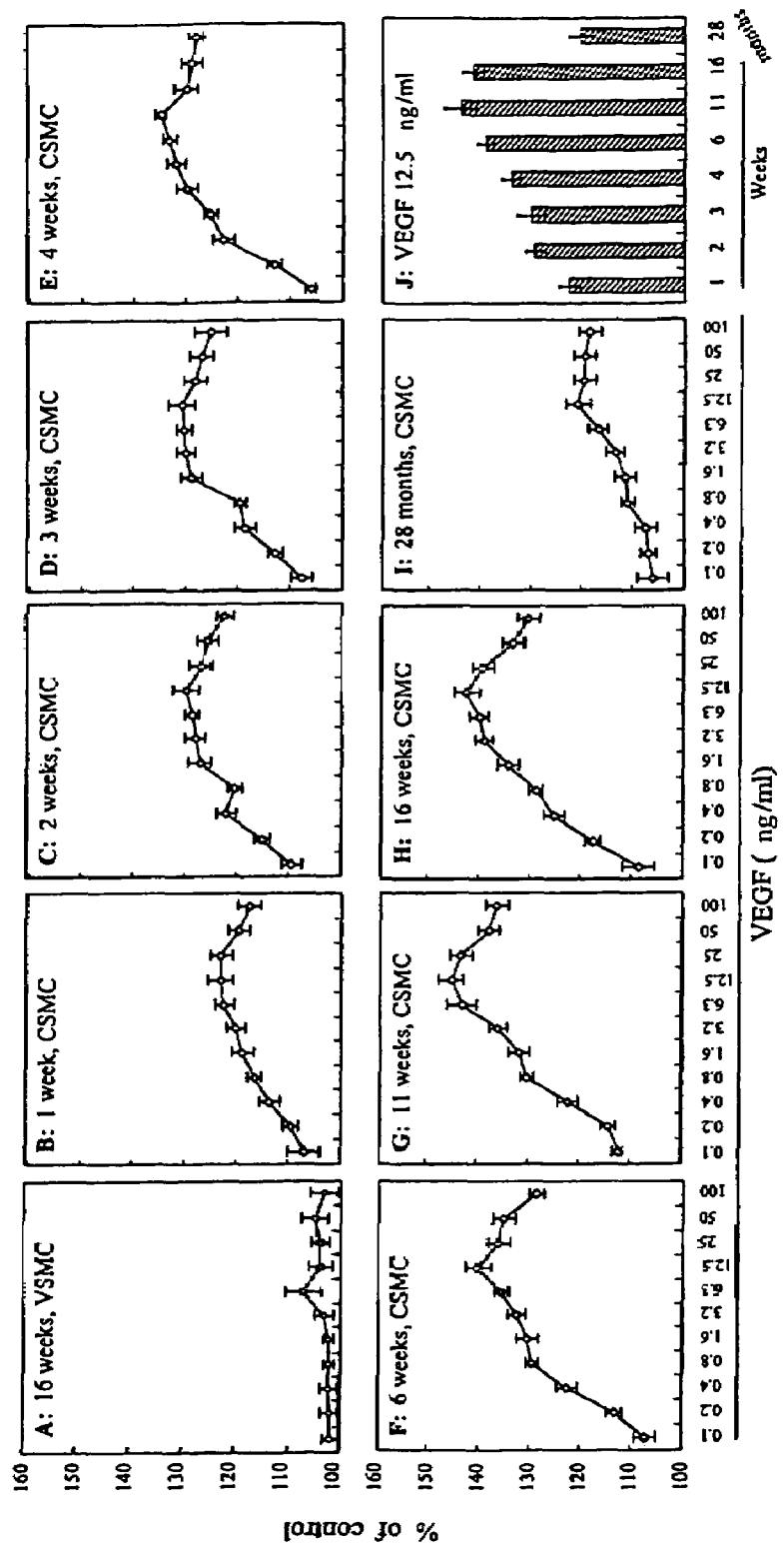
FIG. 3. Effects of VEGF on the growth rates of VSMC and CSMC. Equal numbers (5,000) of VSMC (from 16-weeks-old rats, panel A) and CSMC (from rats of indicated ages, panels B to I) were seeded in each well of 96-well plates and allowed to grow for three days in media containing the indicated concentrations of VEGF. The final numbers of cells were determined with a proliferation assay kit and expressed as optical density ($OD_{490}$ nm) values. These values were converted into % of control (shown on the left of panels A through J) with the value of the growth rate in medium containing no added VEGF being referred to as control (i.e., 100%). Panel J compares the growth rates of CSMC from rats of the indicated ages in media containing the optimal concentration (12.5 ng/ml) of VEGF.
Figure 5:
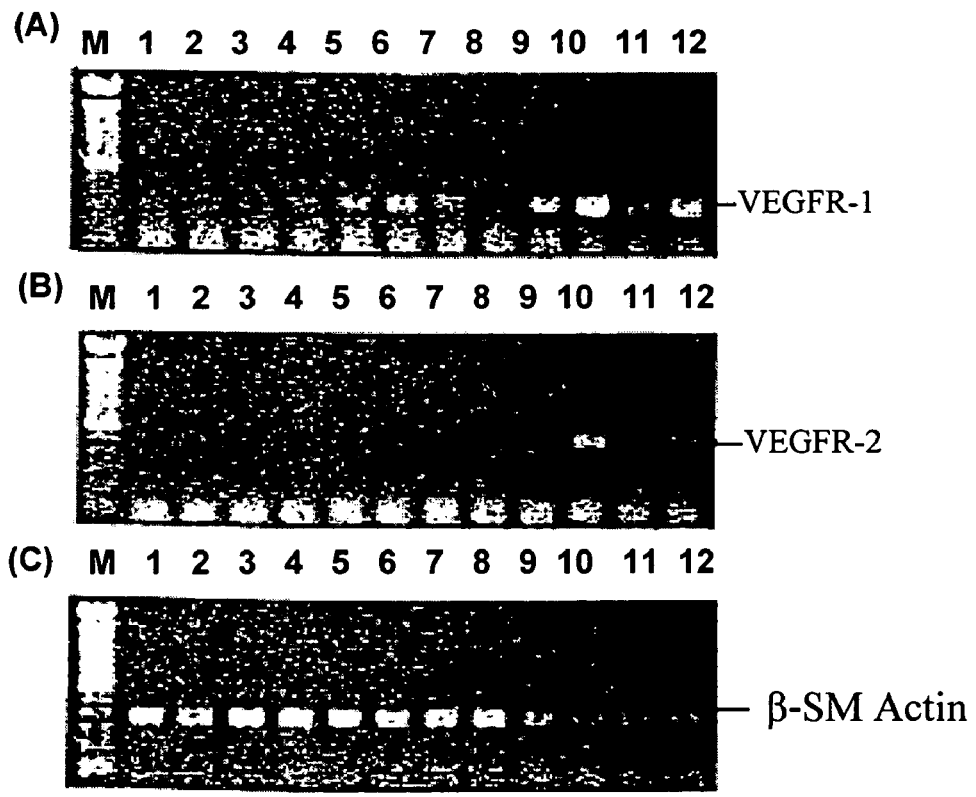
FIG. 5. Identification of VEGFR-1 and VEGFR-2 mRNA expression. RNAs of the following cells and tissues (lanes 1-15) were subjected to RT-PCR with primer pair VEGFR-1s and VEGFR-1a, primer pair VEGFR-2s and VEGFR-2a, and primer pair β-actin-s and β-actin-a (Table 1). The reaction products were electrophoresed in a 1.5% agarose gel and stained with ethidium bromide. The RT-PCR product in each lane was derived from 25 ng (for VEGFR-1 and VEGFR-2) or 1 ng (for β-actin) of total cellular or tissue RNAs. M, 100-bp size marker. Lane 1, CSMC from 1-week-old rats; lane 2, CSMC from 2-weeks-old rats; lane 3, CSMC from 3-weeks-old rats; lane 4, CSMC from 4-weeks-old rats; lane 5, CSMC from 6-weeks-old rats; lane 6, CSMC from 11-weeks-old rats; lane 7, CSMC from 16-weeks-old rats; lane 8, CSMC from 28-months-old rats; lane 9, aorta SMC from 16-weeks-old rats; lane 10, heart of a 16-weeks-old rat; lane 11, aorta of a 16-weeks-old rat; lane 12, corpus cavernosum of a 16-weeks-old rat.

Identification of VEGFR-1 and VEGFR-2 mRNA expression. The above cell proliferation and migration assay results suggested the presence of functional VEGF receptors in CSMC. To verify this, we use RT-PCR to examine the CSMC for the expression of VEGFR-1 and VEGFR-2 mRNAs. As shown in FIG. 5A, CSMC of different-aged rats expressed VEGFR-1 mRNA at different levels, being very low for the young ones (1 to 3 weeks of age) and the very old (28 months of age) and high for the adolescent (4 and 6 weeks of age) and the matured (11 and 16 weeks of age). This pattern of VEGFR-1 mRNA expression is similar to that of VEGF-induced cell proliferation (FIG. 3).

On the other hand, CSMC, regardless of the ages of rats from which they were derived, did not express VEGFR-2 (Lanes 1 to 8, FIG. 5B). This negative result could not have been due to improper RT-PCR conditions or improper primer design because rat heart, aorta, and penis all produced positive results under the same experimental conditions (lanes 10, 11, and 12, FIG. 5B). The positive VEGFR-2 expression in heart, aorta, and penis was most likely derived from vascular endothelial cells that were included in the preparation of these tissue RNAs. It should be pointed out that our rat VSMC were also negative for VEGFR-2 expression (Lane 9, FIG. 5B). This is in agreement with a previous study which reported that SMC of rat carotid arteries express VEGFR-1 but not VEGFR-2. Couper, et al., *Circ. Res.*, 81: 932 (1997).

Figure 6:
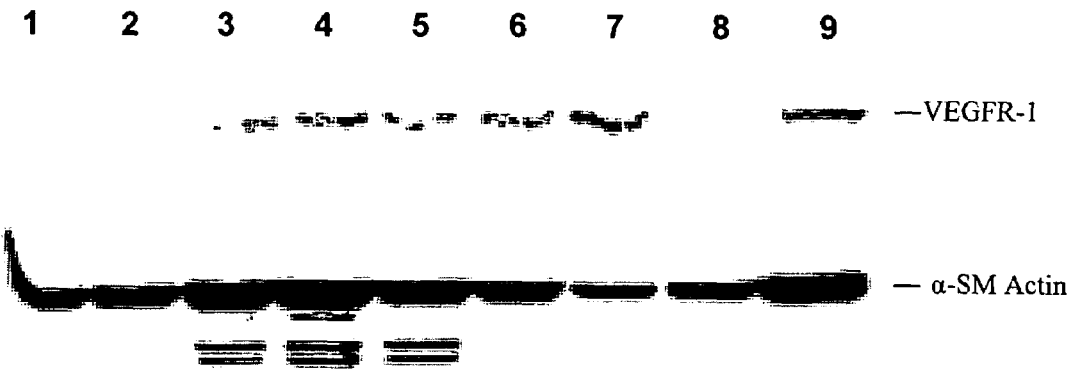
FIG. 6. Identification of VEGFR-1 protein expression. Protein extracts of CSMC from rats of the following ages (lanes 1-8) were electrophoresed in 7.5% SDS-PAGE and then transferred to PVDF membrane. Detection of VEGFR-1 protein on the membrane was performed by the ECL procedure using an anti-VEGFR-1 rabbit serum. Lane 1, 1-week-old; lane 2, 2-weeks-old; lane 3, 3-weeks-old; lane 4, 4-weeks-old; lane 5, 6-weeks-old; lane 6, 11-weeks-old; lane 7, 16-weeks-old; lane 8, 28-months-old.

Identification of VEGFR-1 protein expression. To ascertain that VEGFR-1 protein was indeed expressed in CSMC, we performed immunoblotting experiments using a VEGFR-1-specific antibody. As shown in FIG. 6, VEGFR-1 was detected in CSMC from rats of all ages, and the levels of its expression was very similar to those seen in the results of RT-PCR experiments (FIG. 5A). Therefore, both the expression of VEGFR-1 mRNA and VEGFR-1 protein correlated well with the VEGF-regulated growth rate of CSMC.

Discussion

The erectile function of the penis is that of a vascular organ. Like those of other vascular organs, the development and growth of the penile vasculature are expected to be governed by angiogenic growth factors such as VEGF. Surprisingly, reports concerning VEGF expression in the penis have been scant. In two separate studies, Burchardt et al. reported the identification of novel VEGF splice variants in the penis. Burchardt et al., *Biol. Reprod.*, 60: 398 (1999), Burchardt, et al., *IUBMB Life*, 48: 405 (1999). In another study concerning the expression of various growth factors in the penis, Jung et al. reported the identification of $VEGF_{189}$ mRNA in the penis. Jung, et al., *Int. J. Impotence Res.*, 11: 247 (1999). Our ischemia rat model clearly demonstrated the beneficial effects of VEGF on the restoration of the erectile function following surgical procedures that restricted blood supply to the penis.

We have conducted several experiments (RT-PCR, western blots, immunohistochemical stainings) on the expression of various VEGF forms and their receptors in the penis (unpublished). In trying to interpret the results of those experiments, we were confronted with the question which cell types (smooth muscle, endothelium, nerve, etc.) were the source of a positive gene expression. By using cultures of a single cell type, we were able to show in the present study that CSMC expressed VEGF and VEGFR-1 but not VEGFR-2. We also showed that both the secretion of VEGF and the expression of VEGFR-1 increased with the age of young rats (from 1 to 16 weeks of age) but declined in very old rats (28 months of age).

We are aware of only three previously published reports that studied the effects of VEGF on SMC or expression of VEGF receptors in SMC. First, Brown et al. showed that cultured human uterine SMC expressed both VEGFR-1 and VEGFR-2 and responded to VEGF stimulation in the form of cell proliferation. Brown, et al., *Lab. Invest.*, 76: 245 (1997). These authors also showed that human colon SMC did not express VEGF receptors and did not respond to VEGF stimulation. Secondly, Couper et al. observed high levels of VEGFR-1, but no VEGFR-2, expression in SMC of rat carotid arteries following balloon injury. Couper, et al., *Circ. Res.*, 81: 932 (1997). Thirdly, Grosskreutz et al. showed that cultured bovine aorta SMC expressed both VEGFR-1 and VEGFR-2 and responded to VEGF stimulation in the form of cell migration (but not cell proliferation). Grosskreutz, et al., *Microvasc. Res.*, 58: 128 (1999). In the present study, we used rat aorta SMC for comparison with rat CSMC. We found that, like bovine aorta SMC, rat aorta SMC responded to VEGF stimulation in the form of cell migration but not cell proliferation. However, we could only identify VEGFR-1 but not VEGFR-2 expression in rat aorta SMC. Whether the discrepancy regarding VEGFR-2 expression is due to species difference (bovine verses rat) or other factors (age) needs to be clarified in future studies.

The significance of the proliferative and migratory responses of CSMC toward VEGF is not known. Brown et al. speculated that alterations in expression of VEGF or VEGF receptors may play a role in the pathogenesis of smooth muscle tumors in the uterus. Brown, et al., *Lab. Invest.*, 76: 245 (1997). Grosskreutz et al. proposed that VEGF might have a chemoattractant role in the recruitment of smooth muscle cells during the formation of a blood vessel wall. Grosskreutz, et al., *Microvasc. Res.*, 58: 128 (1999). Because the proliferative effect of VEGF occurred mainly with CSMC of young adult rats (11 weeks of age), it is possible that VEGF at least play a role in maintaining a healthy population of CSMC. As for the migratory effect of VEGF, which occurred mainly with even younger rats (4 weeks of age), we propose that VEGF might play a role in recruiting and/or locating CSMC to the proper sites in the cavernous spaces during adolescence.

In conclusion, we believe our present study has made the following novel observations:
(1) CSMC secreted VEGF, (2) CSMC expressed a VEGF receptor, (3) CSMC exhibited migratory and proliferative responses to VEGF, and (4) CSMC from different-aged rats expressed different levels of VEGF and VEGFR-1 and responded to VEGF at different rates.

References For Example 4

1. Lue, T. F. (2000) New Eng. J. Med. 342(24), 1802-1813.
2. Lee, M.-C., El-Sakka, A., Bakircioglu, E., Lin, C.-S. and Lue, T. F. (2000) J. Urol. 163(4), 198.
3. Achen, M. G., Jeltsch, M., Kukk, E., Mäkinen, T., Vitali, A., Wilks, A. F., Alitalo, K. and Stacker, S. A. (1998) Proc. Nat. Acad. Sci. USA 95(2), 548-553.
4. Joukov, V., Pajusola, K., Kaipainen, A., Chilov, D., Lahtinen, I., Kukk, E., Saksela, O., Kalkkinen, N. and Alitalo, K. (1996) EMBO J. 15(2), 290-298.
5. Maglione, D., Guerriero, V., Viglietto, G., Ferraro, M. G., Aprelikova, O., Alitalo, K., Del Vecchio, S., Lei, K. J., Chou, J. Y. and Persico, M. G. (1993) Oncogene 8(4), 925-931.
6. Olofsson, B., Pajusola, K., Kaipainen, A., von Euler, G., Joukov, V., Saksela, O., Orpana, A., Pettersson, R. F., Alitalo, K. and Eriksson, U. (1996) Proc. Nat. Acad. Sci. USA 93(6), 2576-2581.
7. Yamada, Y., Nezu, J., Shimane, M. and Hirata, Y. (1997) Genomics 42(3), 483-488.
8. Anthony, F. W., Wheeler, T., Elcock, C. L., Pickett, M. and Thomas, E. J. (1994) Placenta 15(5), 557-561.
9. Neufeld, G., Cohen, T., Gengrinovitch, S. and Poltorak, Z. (1999) FASEB J. 13(1), 9-22.
10. Lei, J., Jiang, A. and Pei, D. (1998) Biochim. et Biophys. Acta 1443(3), 400-406.
11. Jingjing, L., Xue, Y., Agarwal, N. and Roque, R. S. (1999) Invest. Ophthal. Vis. Sci., 40(3), 752-759.
12. Cheung, C. Y., Singh, M., Ebaugh, M. J. and Brace, R. A. (1995) Am. J. Obst. Gynecol., 173(3 Pt 1), 753-759.
13. Burchardt, M., Burchardt, T., Chen, M. W., Shabsigh, A., de la Taille, A., Buttyan, R. and Shabsigh, R. (1999) Biol. Reprod. 60(2), 398-404.
14. Pueyo, M. E., Chen, Y., D'Angelo, G. and Michel, J. B. (1998) Exp. Cell Res. 238(2), 354-358.
15. Tischer, E., Mitchell, R., Hartman, T., Silva, M., Gospodarowicz, D., Fiddes, J. C. and Abraham, J. A. (1991) J. Biol. Chem. 266(18), 11947-11954.
16. Claffey, K. P., Wilkison, W. O. and Spiegelman, B. M. (1992) J. Biol. Chem. 267(23), 16317-16322.
17. Goldberg, M. A. and Schneider, T. J. (1994) J. Biol. Chem. 269(6), 4355-4359.
18. Shweiki, D., Neeman, M., Itin, A. and Keshet, E. (1995) Proc. Nat. Acad. Sci. USA 92(3), 768-72.
19. Waltenberger, J., Claesson-Welsh, L., Siegbahn, A., Shibuya, M. and Heldin, C. H. (1994) J. Biol. Chem. 269 (43), 26988-26995.
20. Ortega, N., Hutchings, H. and Plouët, J. (1999) Front. Biosci. 4(4), D141-152.
21. Grosskreutz, C. L., Anand-Apte, B., Duplaa, C., Quinn, T. P., Terman, B. I., Zetter, B. and D'Amore, P. A. (1999) Microvasc. Res. 58(2), 128-136.
22. Brown, L. F., Detmar, M., Tognazzi, K., Abu-Jawdeh, G. and Iruela-Arispe, M. L. (1997) Lab. Invest. 76(2), 245-255.

23. Couper, L. L., Bryant, S. R., Eldrup-Jørgensen, J., Bredenberg, C. E. and Lindner, V. (1997) Circ. Res. 81(6), 932-939.
24. Burchardt, T., Burchardt, M., Chen, M. W., Buttyan, R., de la Taille, A., Shabsigh, A. and Shabsigh, R. (1999) IUBMB Life 48(4), 405-408.
25. Jung, G. W., Kwak, J. Y., Yoon, S., Yoon, J. H. and Lue, T. F. (1999) Int. J. Impotence Res. 11(5), 247-259.

Example 5

The Effect of a Vascular Endothelial Growth factor (VEGF) and Adeno-Associated Brain Derived Neurotrophic Factor (AAV-BDNF) for the Treatment of Erectile Dysfunction Induced by Hypercholesterolemia in a Rat Model Twenty-one Sprague-Dawley rats were used. All rats were fed a 2.5% cholesterol diet with added lard starting at 2 weeks of age for 6 months. The rats were divided into three groups. All groups after two months of a high cholesterol diet underwent serum evaluation of cholesterol and intracavernous injection of saline or treatment. Group 1, the control group, received intracavernous injection of saline, group 2, the VEGF group, received intracavernous injection of 4 ug of VEGF, and group 3, the AAV-BDNF group received 15 ug of BDNF. After six months of cholesterol diet and 4 months of treatment, all rats were subjected to cavernous nerve electrostimulation, cavernosometry with intracavernous papaverine injection, and infusion cavernosometry with heparinized saline to measure erectile function.

Results

Serum cholesterol levels were significantly higher in animals fed the high cholesterol diet. Systemic arterial pressure was not significantly different among the different groups. During electrostimulation of the cavernous nerve, peak sustained intracavernous pressure was significantly lower in the cholesterol only group (50+/-23 cm. $H_2O$) compared to the control and the VEFG and AAV-BDNF groups. During the pharmacologic erection phase of the cavernosometry, the VEGF and BDNF treated groups had significantly higher sustained intracavernous pressures in comparison to the high cholesterol controls. No difference was noted with respect to the infusion cavernosometry assessing venous leak when comparing the controls and the treated groups.

Conclusion

Rats developed erectile dysfunction after being fed a high cholesterol diet (2.5% with lard) for 6 months. VEGF and AAV-BDNF seem to reverse the erectile dysfunction caused by high cholesterol diet.

Example 6

The Effect of Intracavernous Vascular Endothelial Growth Factor (VEGF) on a Rodent Model of Neurogenic Erectile Dysfunction.

Objective: To test the hypothesis that intracavernous injection of VEGF can facilitate regeneration of the cavernous nerve and restore erectile function after cavernous nerve injury in rats.

Materials and Methods: Seventeen 3 months old Sprague Dowry rats underwent bilateral freezing of the cavernous nerves with a thermocouple immersed in liquid nitrogen. Through an abdominal incision both cavernous nerves were isolated lateral to the prostate and frozen with thermocouple for one minute twice (temperature cycle $-130°$ C. to $-3°$ C.). Minutes later, intracavernous injection of saline (n=7) or VEGF, 4 ug, (n=9) was given. Three months later, all rats underwent re-exploration and electrostimulation of the cavernous nerves to assess erectile function. Eight additional rats underwent exploration only (sham group).

Results

The maximal intracavernous pressure in the rats underwent sham operation was 90±8.15 cm H2O. The maximal intracavernous pressure of both the saline treated group (39.29±5.02 cm $H_2O$) and the VEGF treated group (72.78+ 10.87 cm $H_2O$) were lower than the sham group. Nevertheless, the intracavernous pressure in the VEGF treated group was significantly higher than the saline treated group (p=0.0389).

Conclusion

Although VEGF is known as an angiogenetic factor, previous reports have suggested that it may also be neuroprotective and neurotrophic. Our study shows that intracavernous injection of VEGF significantly facilitated recovery of erectile function after bilateral cavernous nerve injury. If further studies confirmed that VEGF enhances both angiogensis and neural regeneration, intracavernous VEGF therapy may be the treatment of choice in helping patient recover potency after radical prostatectomy or cryoablation of the prostate.

The above examples are included for illustrative purposes only and is not intended to limit the scope of the invention. Since modifications will be apparent to those of skill in this art, it is intended that this invention be limited only by the scope of the appended claims.

The invention claimed is:

1. A method for preventing or treating male erectile dysfunction, which method comprises administering to a male mammal for whom such prevention or treatment is needed or desirable, an effective amount of
   basic fibroblast growth factor (bFGF) protein,
   thereby preventing or treating said male erectile dysfunction in said mammal.

2. The method of claim 1, wherein the mammal is a human and the bFGF protein is of human origin.

3. The method of claim 1, wherein the bFGF protein is administered by intracavernous injection, subcutaneous injection, intravenous injection, intramuscular injection, intradermal injection, or topical administration.

4. The method of claim 1, wherein the bFGF protein is administered via a liposome.

5. The method of claim 1, for preventing or treating male erectile dysfunction wherein the male erectile dysfunction is erectile dysfunction induced by or secondary to nerve dysfunction, arterial insufficiency, venous leakage, hormonal insufficiency, drug use, surgery, chemotherapy or radiation.

6. The method of claim 1, wherein the bFGF protein is administered by intracavernous injection.

7. The method of claim 1, wherein the dysfunction is induced by hypercholesterolemia or induced by a cavernous nerve injury.

8. The method of claim 1, wherein the bFGF protein is administered at about 10-200 mcg/70 Kg body weight about once every two to six months.

9. The method of claim 1, which further comprises administering an effective amount of vascular endothelial growth factor (VEGF) protein.

10. The method of claim 9, wherein the VEGF protein is administered at about 10-200 mcg/70 Kg body weight about once every two to six months.

11. The method of claim 1, which further comprises administering an effective amount of brain derived neurotrophic factor (BDNF) protein.

12. The method of claim 11, wherein the BDNF protein is administered at about 10-200 mcg/70 Kg body weight about once every two to six months.

13. The method of claim 9, which further comprises administering an effective amount of brain derived neurotrophic factor (BDNF) protein.

14. The method of claim 13, wherein the BDNF protein is administered at about 10-200 mcg/70 Kg body weight about once every two to six months.

15. The method of claim 1, wherein the bFGF is in the form of a pharmaceutical composition.

16. The method of claim 15, wherein the composition further comprises a pharmaceutically acceptable carrier or excipient.

* * * * *

UNITED STATES PATENT AND TRADEMARK OFFICE
CERTIFICATE OF CORRECTION

PATENT NO. : 7,485,311 B2  Page 1 of 1
APPLICATION NO. : 10/806515
DATED : February 3, 2009
INVENTOR(S) : Tom F. Lue et al.

It is certified that error appears in the above-identified patent and that said Letters Patent is hereby corrected as shown below:

At column 1, lines 19-23 please delete "This invention is supported by Grant No. DK45370 and DK51374 of the National Institutes of Health. The United States government may have certain rights in this invention." and replace with
--This invention was made with government support under Grant No. DK45370 and DK51374 awarded by the National Institutes of Health. The Government has certain rights in the invention.--

Signed and Sealed this

Twenty-first Day of April, 2009

JOHN DOLL
*Acting Director of the United States Patent and Trademark Office*